United States Patent
Tuchman

(10) Patent No.: US 7,947,503 B2
(45) Date of Patent: May 24, 2011

(54) MONITOR AND METHODS FOR CHARACTERIZING AIRBORNE PARTICULATES

(75) Inventor: Donald P. Tuchman, Pittsburgh, PA (US)

(73) Assignee: The United States of America as represented by the Department of Health and Human Services, Washington, DC (US)

( * ) Notice: Subject to any disclaimer, the term of this patent is extended or adjusted under 35 U.S.C. 154(b) by 413 days.

(21) Appl. No.: 11/922,381

(22) PCT Filed: Jun. 14, 2006

(86) PCT No.: PCT/US2006/023166
§ 371 (c)(1),
(2), (4) Date: Dec. 14, 2007

(87) PCT Pub. No.: WO2006/138375
PCT Pub. Date: Dec. 28, 2006

(65) Prior Publication Data
US 2009/0081804 A1    Mar. 26, 2009

Related U.S. Application Data

(60) Provisional application No. 60/691,564, filed on Jun. 17, 2005.

(51) Int. Cl.
*G01N 33/24* (2006.01)
(52) U.S. Cl. .......... 436/28; 436/160; 436/177; 422/534; 422/535; 73/865; 177/210 FP; 177/210 R
(58) Field of Classification Search .................... 422/101
See application file for complete search history.

(56) References Cited

U.S. PATENT DOCUMENTS

| | | | |
|---|---|---|---|
| 3,744,297 A | 7/1973 | Hanson et al. | |
| 3,926,271 A | 12/1975 | Patashnick | |
| 4,178,794 A | * 12/1979 | Jugle et al. | ................. 73/863.25 |
| 4,391,338 A | 7/1983 | Patashnick et al. | |

(Continued)

FOREIGN PATENT DOCUMENTS

GB        2372102 A       8/2002

(Continued)

OTHER PUBLICATIONS

Haney, R. A. "Diesel particulate exposures in underground mines." Mining Engineering (1992) 44 p. 173-176.*

(Continued)

*Primary Examiner* — Yelena G Gakh
*Assistant Examiner* — Christopher A Hixson
(74) *Attorney, Agent, or Firm* — Klarquist Sparkman, LLP

(57) ABSTRACT

A dust monitor is disclosed that is suitably deployed in dusty environments and capable of providing near real-time indications of exposure to airborne particulates. The monitor includes a filter and filter assembly made of materials that do not interfere with subsequent instrumental (such as spectrometric) analysis for detecting and/or quantitating an analyte. In some disclosed embodiments, the filter is made of nylon or other material that is readily subjected to thermal destruction prior to spectrometric analysis. The dust monitor also includes a humidity correction feature that permits the filter to be made of ashable organic materials even if those materials are not highly hydrophobic. Transport devices are provided for shipment of the filter and/or filter assembly to an analytical laboratory which prevent loss of particulate matter and which facilitate an accurate analysis procedure.

27 Claims, 9 Drawing Sheets

U.S. PATENT DOCUMENTS

| | | | |
|---|---|---|---|
| 4,677,863 A | 7/1987 | Gay et al. | |
| 4,696,181 A | 9/1987 | Rupprecht et al. | |
| 5,290,705 A | 3/1994 | Davis | |
| 5,349,844 A | 9/1994 | Lilienfeld | |
| 5,470,757 A | 11/1995 | Gagnon et al. | |
| 5,488,203 A | 1/1996 | Hassel et al. | |
| 5,604,335 A | 2/1997 | Isahaya | |
| 5,717,147 A | 2/1998 | Basch et al. | |
| 5,764,355 A | 6/1998 | Gagnon et al. | |
| 5,898,114 A * | 4/1999 | Basch et al. | 73/863.23 |
| 6,016,688 A | 1/2000 | Hiss et al. | |
| 6,055,052 A | 4/2000 | Lilienfeld | |
| 6,080,939 A | 6/2000 | Hassel | |
| 6,114,964 A | 9/2000 | Fasano | |
| 6,122,054 A | 9/2000 | Ence | |
| 6,205,842 B1 | 3/2001 | Patashnick et al. | |
| 6,285,730 B1 | 9/2001 | Barnes | |
| 6,422,060 B1 | 7/2002 | Patashnick et al. | |
| 6,439,027 B1 | 8/2002 | Hiss, III | |
| 6,444,927 B1 | 9/2002 | Korpi | |
| 6,465,749 B1 | 10/2002 | Kurz | |
| 6,502,450 B1 | 1/2003 | Pataschnick et al. | |
| 6,762,060 B1 | 7/2004 | Zaromb | |
| 6,784,381 B2 | 8/2004 | Korpi | |
| 7,111,496 B1 | 9/2006 | Lilienfeld et al. | |
| 7,197,911 B1 | 4/2007 | Lilienfeld | |
| 7,285,736 B2 | 10/2007 | Korpi | |
| 2004/0163540 A1 * | 8/2004 | Mori et al. | 96/134 |

FOREIGN PATENT DOCUMENTS

WO     WO91/01487 A     2/1991

OTHER PUBLICATIONS

Lockhart, L. B. et al. "Filter pack technique for classifying radioactive aerosols by particle size." Naval Research Lab Report Abstract, retreived online from <http://oai.dtic.mil/oai/oai?verb=getRecord&metadataPrefix=html&identifier=AD0649728> on May 21, 2010, report published Mar. 1, 1967.*

International Search Report and Written Opinion of the International Searching Authority, mailed Nov. 23, 2006, for corresponding International Application No. PCT/US2006/023166.

Anderson, "Free Silica Analysis of Environmental Samples—A Critical Literature Review," Am. Ind. Hyg. Assoc. J., 36(10):767-778, 1975.

Asbach et al., "Online Monitor for Measurement of Real Airborne Particle Mass Concentrations," Proceedings of QA/QC in the Field of Emission and Air Pollution Control Conference, Prague, pp. 191-198, May 21-23, 2003.

Beaulieu et al., "Mesure de poussières dans l'air ambian: Correction de la masse des membranes filtrantes d'ester de cellulose en function de l'humidité atmosphérique," Analusis, 14, No. 2:74-78, 1986.

Cahn, Lee, "Technical Note—Dynamic Weight Change of a Membrane Filter with Humidity," Materials Res. & Stan., 3(5):377, May 1963.

Cantrell, "Status of a Tapered Element, Oscillating Microbalance-Based Continuous Respirable Coal Mine Dust Monitor," Appl. Occup. Environ. Hyg., 11(7):624-629, Jul. 1996.

Charell et al., "Characteristics of Water Adsorption on Air Sampling Filters," Am. Ind. Hyg. Assoc. J., 42(5):353-360, 1981.

Charron et al., "Quantitative Interpretation of Divergence Between $PM_{10}$ and $PM_{2.5}$ Mass Measurement by TEOM and Gravimetric (Partisol) Instruments" Atmospheric Environ., 38:415-423, 2004.

Chung et al., "Comparison of Real-Time Instruments Used to Monitor Airborne Particulate Matter," J. Air & Waste Manage. Assoc., 51:109-120, 2001.

Drolet and Perrault, "Applications of a Mathematical Model of Weight Correction for Several Membranes Used for Dust Sampling," presented at the A.H.I.C. (American Health Information Community, Montreal, Canada, 1987.

Foster et al., "Quantitative Determination of Crystalline Silica in Respirable-Size Dust Samples by Infrared Spectrophotometry," Analyst, 109:1117-1127, Sep. 1984.

Freedman et al., "On-Filter Analysis of Quartz in Respirable Coal Dust by Infrared Absorption and X-Ray Diffraction," Am. Ind. Hyg. Assoc. J., 35(7):411-418, 1974.

Gilbert and Clark, "Measurement of Particulate Matter from Diesel Engine Exhaust Using a Tapered Element Oscillating Microbalance," Int. J. Engine Research, 2(4):277-287, Nov. 2001.

Gilbert, Marcus (Thesis Paper) "Investigation Into the Use of a Tapered Element Oscillating Microbalance for Real-Time Particulate Measurement," College of Engineering and Mineral Resources, West Virginia University; 86 pgs, 2002.

http://www.hazdust.com/hd1003.php, "Haz-Dust IV Personal Real-Time Dust Monitor," Environmental Devices Corporation, 2pgs, retrieved Nov. 5, 2009.

http://www.internationalcrystal.net/realcryt.htm, "Real Crystal IR Sample Cards," International Crystal Laboratories—Supplies and Accessories for Spectroscope, 7 pgs, retrieved Jun. 12, 2006.

http://www.internationalcrystal.net/000.htm, "IR Sample Cards and Kits," International Crystal Laboratories, 2 pgs, retrieved Jun. 12, 2006.

http://wwww.skcshopping.com/ProductDetails.asp-?ProductCode=770-4004K&Show=ExtInfo, "Haz-Dust IV, Personal Monitor Kit, 110V, Logging," SKC, Inc., 6 pgs, retrieved Nov. 5, 2009.

http://wwww.skcshopping.com/ProductDetails.asp-?ProductCode=225-01-02&Show=ExtInfo, "Cyclone, Aluminum, 37mm—Respirable Dust Aluminum Cyclone," SKC, Inc., 6 pgs., retrieved Nov. 5, 2009.

http://www.teom.com/products/ambprod/amb1400/metals.htm, TEOM Series 1400a Monitor Heavy Metals Analysis, Thermo Electron Corporation—rp Air Quality Instruments, 1 pg, retrieved Jun. 12, 2006.

Hogrefe et al., "Development, Operation and Applications of an Aerosol Generation, Calibration and Research Facility," Aerosol Sci. & Tech., 38(12):196-214, 2004.

Jalani et al., "TEOM—A Novel Technique for Investigating Sorption in Proton-Exchange Membranes" J. Membrane Sci., 254:31-38, 2005.

Jalani et al., "Synthesis and Characterization of Nafion®-M)$_2$ (M=Zr, Si, Ti) Nanocomposite Membranes for Higher Temperature PEM Fuel Cells" Electrochimica Acta, 51:553-560, 2005.

Jaques et al., " Field Evaluation of the Differential TEOM Monitor for Continuous $PM_{2.5}$ Mass Concentrations" Aerosol Sci. & Tech., 38(S1):49-59, 2004.

Jarrett et al., "Evaluation and Correction of Moisture Adsorption and Desorption From a Tapered Element Oscillating Microbalance" Powder Tech., 119:215-228, 2001.

Jones et al., "Microscopy and Chemistry of Particles Collected TEOM Filters: Swansea, South Wales, 1998-1999" Atmospheric Environ., 35:3573-3583, 2001.

Kissell et al., "Test Report on the Machine-Mounted Continuous Respirable Dust Monitor" Chapter 38, Proceedings of the $7^{th}$ International Mine Ventilation Congress, Cracow, Poland, pp. 253-260, Jun. 17-22, 2001.

Knight, "X-Ray Diffraction Analysis of Mine Airborne Dust—An Interference Problem at Hemlo Gold Mines," Am. Ind. Hyg. Assoc. J., 50(6):293-297, 1989.

Li et al., "Ashing and Microwave Digestion of Aerosol Samples With a Polypropylene Fibrous Filter Matrix" Analytica Chimica Acta., 482:129-135, 2003.

MSA, Data Sheet 08-00-14, Gravimetric Dust Sampling Kit, 2 pgs, 1987.

Madsen et al., "Review of Quartz Analytical Methodologies: Present and Future Needs" Appl. Occup. Environ. Hyg., 10(12):991-1002, Dec. 1995.

D. Mark, "Problems Associated with the Use of Membrane Filters for Dust Sampling When Compositional Analysis is Required" Ann. Occup. Hyg., 17:35-40, 1974.

Meyer et al., "Development of a Sample Equilibration system for the TEOM Continuous PM Monitor," J. Air & Waste Manage. Assoc., 50:1345-1349, 2000.

Miles, "Issues and Controversy: The Measurement of Crystalline Silica; Review Papers on Analytical Methods," Am. Ind. Hyg. Assoc. J., 60(3):396-402, 1999.

"MSHA's Procedure for Determining Quartz Content of Respirable Coal Mine Dust," U.S. Dept. of Labor—Mine Safety and Health Administration, Informational Report IR 1152, 16 pgs, 1984.

Miola and Ramani, "Quartz Content in Bulk-Coal, Host-Rock and Airborne Dust Samples: A Comparative Study of IR and XRD Procedures," Transactions of Soc. Min. Metall. & Explor., vol. 298:1845-1850, 1995.

National Institute for Occupational Safety and Health, "Method 7500—Silica, Crystalline, by XRD (filter redeposition)," NIOSH Man. of Analy. Mthds., 9 pgs (Mar. 2003).

National Institute for Occupational Safety and Health, "Method 7501—Silica, Amorphous," NIOSH Man. of Analy. Mthds., 8 pgs (Mar. 2003).

National Institute for Occupational Safety and Health, "Method 7601—Silica, Crystalline, by VIS," NIOSH Man. of Analy. Mthds., 6 pgs (Mar. 2003).

National Institute for Occupational Safety and Health, "Method 7602—Silica, Crystalline, by IR (KBr pellet)," NIOSH Man. of Analy. Mthds., 6 pgs (Mar. 2003).

National Institute for Occupational Safety and Health, "Method 7603—Quartz in Coal Mine Dust, by IR (redeposition)," NIOSH Man. of Analy. Mthds., 7 pgs (Mar. 2003).

Ojima, "Determining of Crystalline Silica in Respirable Dust Samples by Infrared Spectrophotometry in the Presence of Interferences," J. Occup. Health, 45:94-103, 2003.

Okrent, "Optimization of a Third Generation TEOM® Monitor for Measuring Diesel Particulate in Real-Time," Society of Automotive Engineers (SAE) Technical Paper Series—980409, International Congress and Exposition, Detroit, Michigan, 8 pgs, Feb. 23-26, 1998.

Omega Specialty Instrument Co., Air Sampling Media and Accessories for Industrial Hygiene, Sales Brochure, 3 pgs, 1996-97.

Operating Manual—TEOM Series 1400a—Ambient Particulate (PM-10) Monitor (AB Serial Numbers), Revision B, R&P Part No. 42-003347; Rupprecht & Patashnick Co., Inc., May 1996.

Operating Manual—TEOM Series 3600/3700—Personal Dust Monitor, Revision A, R&P Part No. 42-009904; Rupprecht & Patashnick Co., Inc., Sep. 2004.

Pall Gelman Sciences, The Filter Book—the ultimate laboratory filtration and separations reference, 5 pgs, 1998.

Patashnick and Rupprecht, "Personal Dust Exposure Monitor Based on the Tapered Element Oscillating Microbalance," A mining research contract report, Contract H0308106, U.S. Dept. of the Interior, Bureau of Mines, 89 pgs, Apr. 1983.

Patashnick and Rupprecht, "Continuous PM-10 Measurements Using the Tapered Element Oscillating Microbalance," J. Air & Waste Manage. Assoc., 41:1079-1083, 1991.

Patashnick, Letters to the Editor, J. Air & Waste Manage. Assoc., 48:195-200, 1998.

Patashnick et al., "Development of a Reference Standard for Particulate Matter Mass in Ambient Air," Aerosol Sci. & Tech., 34:42-45, 2001.

Pataschnick et al., "Tapered Element Oscillating Microbalance Technology," Mine Ventilation, De Souza (ed), Proceedings of the North American/Ninth US Mine Ventilation Symposium, Kingston, Ontario, Canada, pp. 625-631, Jun. 8-12, 2002.

Pickard et al., "A Comparison of X-Ray Diffraction and Infra-Red Spectrophotometric Methods for the Analysis of α-Quartz in Airborne Dusts," Ann. Occup. Hyg., 29(2):149-167, 1985.

Ramani et al., "Quartz Analysis in Coal Mine Samples: Comparison of XRD and P-7 Methods" Chapter 30, Proceedings of the 5$^{th}$ U.S. Mine Ventilation Symposium, West Virginia University, Morgantown, West Virginia, pp. 234-243, Jun. 3-5, 1991.

SKC West, Inc., "2001 Comprehensive Catalog & Air Sampling Guide—The Essential Reference for Air Sampling," Sales Brochure, 4 pgs, 2001.

Schwartz et al., "Chapter R—Determination of Airborne Crystalline Silica," National Institute for Occupational Safety and Health, NIOSH Man. of Analy. Mthds., 260-280, Mar. 15, 2003.

3M Sales Brochure, "Disposable IR Cards," 4 pgs, 1994.

3M News Release, "New IR Cards Analyze Quantitative Samples Effectively Without Messy Cleanup," 1 pg, Mar. 1, 1996.

TEOM® Series 1400a Monitor and Partisol™ Sampler: Technical Note 1—Heavy Metals Analysis, Rupprecht & Patashnick Co., Inc., 4 pgs, Jan. 1995.

TEOM® Series 1400a Ambient Particulate Monitor, Real-Time True Mass Measurement of Suspended Particulate Matter as PM-10, PM-2.5, PM-1 and TSP, Air Monitors Limited—Rupprecht & Patashnick Co., Inc., Sales Brochure, 4 pgs, Sep. 1999.

Tuchman et al., "Implementing Infrared Determination of Quartz Particulates on Novel Filters for a Prototype Dust Monitor," J. Environ. Monit., 10:671-678, 2008.

U.S. Dept. of Health and Human Services, Centers for Disease Control and Prevention, National Institute for Occupational Safety and Health, "Report of Investigations 9663—Performance of a New Personal Respirable Dust Monitor for Mine Use," 25 pgs, Jun. 2004.

U.S. Dept. of Labor, Mine Safety and Health Admin., Pittsburgh Safety and Health Technology Center, "X-Ray Diffraction Determination of Quartz and Cristobalite in Respirable Mine Dust," MSHA P-2, pp. 1-22, Mar. 2002.

U.S. Dept. of Labor, Occupational Safety & Health Admin., "Quartz Analytical Method (P-7), Infrared Determination of Quartz in Respirable Coal Mine Dust," www.osha.gov.index.html, 9 pgs, Accessed on Nov. 11, 2009.

Vander Kolk, "Quartz Analysis of Respirable Dust by X-Ray Diffraction," Ind. Health Foundation, Inc., Pittsburg, PA, pp. 56-68, Mar. 1975.

Volkwein and Thimons, "New Tools to Monitor Personal Exposure to Respirable Coal Mine Dust," Chapter 23, Proceedings of the 7$^{th}$ International Mine Ventilation Congress, Cracow, Poland, pp. 143-150, Jun. 17-22, 2001.

Volkwein et al., "Performance of a Prototype Personal Dust Monitor for Coal Mine Use," Mine Ventilation, De Souza (ed), Proceedings of the North American/Ninth U.S. Mine Ventilation Symposium, Kingston, Ontario, Canada, pp. 633-639, Jun. 8-12, 2002.

Volkwein et al., "Implementing a New Personal Dust Monitor as an Engineering Tool," Coal Age, 109(12):26-29, Dec. 2004.

Webber, Coloring of Plastics—A Volume in the SPE Monograph Series, pp. 10-13, 34-69, 107-111, 127-133, 136-143, 175-185, and 204-215, 1979.

Whitby et al., "Real-Time Diesel Particulate Measurement Using a Tapered Element Oscillating Microbalance," Society of Automotive Engineers (SAE) Technical Paper Series—820463, International Congress and Exposition, Detroit, Michigan, 18 pgs, Feb. 22-26, 1982.

Whitby et al., "Second Generation TEOM Filters—Diesel Particulate Mass Comparisons between TEOM and Conventional Filtration Techniques," Society of Automotive Engineers (SAE) Technical Paper Series—850403, International Congress and Exposition, Detroit, Michigan, 17 pgs, 1985.

Williams et al., "Evaluation of the TEOM Dust Monitor," Bureau of Mines Information Circular—IC 9119, United States Dept. of the Interior, 1986.

* cited by examiner

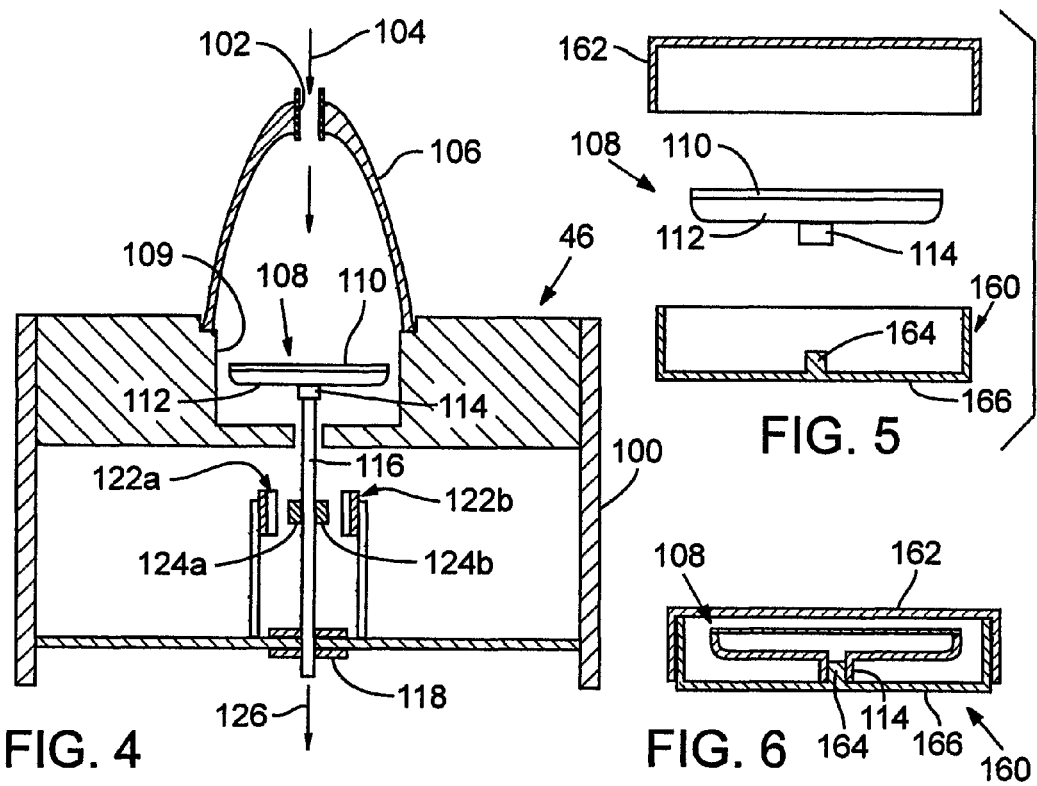
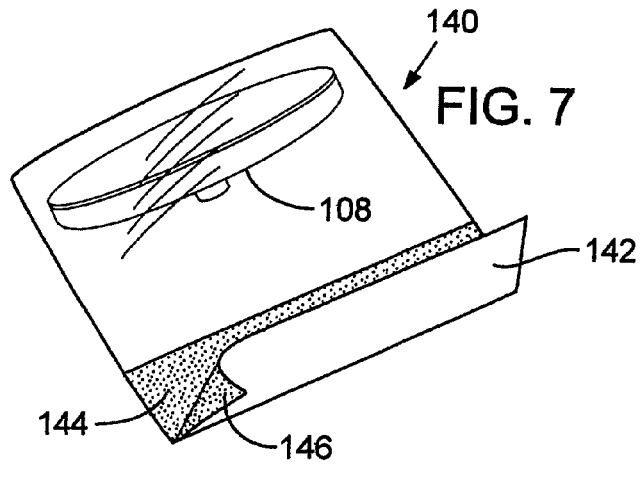
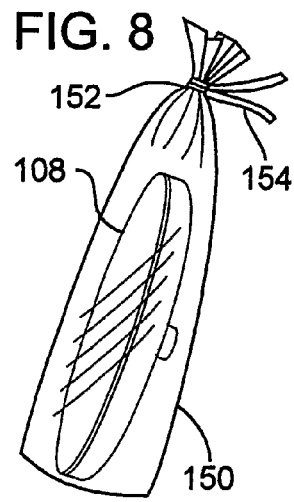

MONITOR AND METHODS FOR CHARACTERIZING AIRBORNE PARTICULATES

CROSS-REFERENCE TO RELATED APPLICATIONS

The present application is the U.S. National Stage of International Application No. PCT/US2006/023166, filed Jun. 14, 2006, which claims the benefit of U.S. Provisional Application No. 60/691,564, filed Jun. 17, 2005, which is incorporated herein by reference.

GOVERNMENT INTERESTS

This invention was made by The National Institute for Occupational Safety and Health, Centers for Disease Control and Prevention, an agency of the United States Government.

FIELD OF THE DISCLOSURE

A dust monitor and related methods are disclosed that are capable of detecting and/or quantitating particulates in an environment, such as particulate concentration in ambient air, and identifying and/or quantitating at least one component of the collected particulates. For example, the monitor is a personal dust monitor worn by workers in dusty environments (such as mines) where dust exposure levels are monitored to avoid health problems and the presence of injurious materials in the dust is determined.

BACKGROUND

Because the lungs are a major interface between the body and its environment, airborne particulates can present health risks to workers in dusty environments. Well known examples of occupationally related pulmonary diseases include coal worker's pneumoconiosis (CWP) induced by exposure to coal dust, silicosis induced by exposure to particles of crystalline silicon dioxide (usually encountered in nature as quartz), and asbestosis caused by exposure to environmental asbestos particles. To reduce the incidence of severe long-term health effects of such exposures, occupational regulations mandate monitoring exposure to particulates in certain work environments.

For example, the Federal Coal Mine Health and Safety Act of 1969 and the Federal Mine Safety and Health Act of 1977 mandated measurement of personal exposure to coal mine dust in the United States. A number of air sampling devices have evolved in response to this type of requirement. A common approach is to use small cyclone air samplers (such as those available through Mine Safety Appliances Co., Pittsburgh, Pa., or SKC, Inc., Eighty Four, Pa.) that can be placed in the work environment or attached to a worker. The cyclone separates smaller respirable particles from larger nonrespirable particles, and collects the respirable particles on a filter for subsequent gravimetric analysis.

The collection of dust particles for subsequent gravimetric analysis can provide an indication of a total particulate exposure over the collection period, but this technique is unable to provide real-time measurements of dust exposure as it occurs. Over the last few decades, several methods have been developed to provide a continuous direct reading of airborne particulate mass concentration. These techniques have included light scattering nephelometry, absorption photometry, beta radiation attenuation (in which beta radiation is attenuated by interaction with electrons in atoms of particulates), measurement of a pressure differential across a sampling tube into which dust particles are drawn and collected (as in U.S. Pat. No. 6,401,520), and resonance frequency decrement.

Resonance frequency decrement devices provide a mass in combination with an energy storage device (such as a spring, or electromagnetic equivalent) that oscillates the mass harmonically at its natural resonance frequency, which is typically proportional to the square root of the ratio of the system stiffness constant and its mass. As this mass increases (during particle collection), the system resonant frequency diminishes. This frequency decrement is a measure of collected particle mass. Examples of this technique (which are further described in U.S. Pat. No. 5,349,844) include an oscillating wire or ribbon used as a particle impaction surface, a quartz crystal piezo-balance, a tapered element oscillating microbalance (TEOM®), and an oscillating filter tape monitor. An advantage of resonant mass monitoring devices is that they provide a continuous direct mass sensing technique with the closest approximation to a reference gravimetric method.

The TEOM® technique was pioneered by Rupprecht & Patashnick Co. (now part of Thermo Electron Corp., pending part of Thermo Fisher Scientific, Inc.) as illustrated in U.S. Pat. No. 3,926,271. In that early approach, the microbalance had a tapered tubular element clamped at one end while the other end was free to vibrate a mass measurement platform. The tapered tubular element was set into oscillation and a feedback system maintained the oscillation. A change of mass on the oscillating platform was determined by measuring the resonant frequency of the tapered tubular element, which changed in mathematical relationship to the mass loading of the tapered tubular element.

A variety of resonance frequency microbalances have been developed in recent years. For example, U.S. Pat. No. 5,349,844 disclosed a resonance frequency microbalance in which a particulate collection filter membrane was oscillated perpendicular to the plane of the filter. In other work, the Rupprecht & Patashnick (R&P) TEOM® has also been developed, in one case into a device that can be used for EPA-required monitoring of particulate concentration in outdoor environments (Patashnick and Rupprecht, *J. Air Waste Management Assoc.* 41:1079, 1991). TEOMs may additionally be adapted for use in a variety of settings, including workplaces. A TEOM® monitor draws in an air sample that is typically heated to about 45° C. to reduce relative humidity, and particles are subsequently collected on a Teflon® and fiberglass filter that is held by and oscillates with a mounting platform on the tip of a glass or metal tube. The specialized Teflon® and fiberglass filter of a TEOM® monitor has been designed to provide a very hydrophobic matrix that minimizes the collection of airborne moisture that may otherwise collect on the filter and provide an inaccurately high particulate mass determination.

A recent embodiment of the R&P TEOM® device is the battery-operated Series 3600 Personal Dust Monitor (PDM) which is contained in a compact housing that can be attached to a worker's belt. The PDM separates smaller particles of the respirable size range from larger particles that would less readily reach the lungs when inhaled. The air carrying respirable particles is then flowed through a hydrophobic filter on the mounting platform where the particulate matter is collected, and its mass is determined by a decrement of resonance oscillation of the TEOM.

Although such microbalances are able to accurately determine a mass of collected particulates, they are unable to chemically identify the particles that are collected and measured. For example, it is sometimes helpful to determine the mass concentration of quartz particles in coal mine dust particles of mixed composition because of the increased risk of disease associated with quartz dust exposure. At the present time, the chemical identification of particulates is accomplished by their collection through a separate device (such as a cyclone) on a filter that is then ashed and subjected to spectroscopic analysis. An example of a technique for analysis of quartz in coal mine dust is found in the NIOSH Manual of Analytical Methods (NMAM), Fourth Edition, Method 7603. Another quartz analytical method for the infrared determination of quartz in respirable coal mine dust is provided in Method P-7 from the Mine Safety and Health Administration (MSHA).

SUMMARY OF THE DISCLOSURE

Unfortunately, it has not been possible to perform certain advantageous types of accurate spectroscopic analysis on the filters used in existing oscillating microbalances because the filters in those devices (such as the TEOM® monitor) have been specially designed to provide a hydrophobic substrate that collects as little moisture as possible on the filter. These specialized filters are made of Teflon® and fiberglass, and their associated mounting platforms sometimes include inorganic materials such as titanium dioxide ($TiO_2$) pigments. These materials can not be readily subjected to thermal or chemical destruction that is the first step in many instrumental analytical methods such as spectroscopy. For example, the filter and/or its mounting platform are not readily subject to low-temperature ashing. Even if the platform or filter is destroyed, it may contain inorganic materials that can interfere with spectroscopic analysis of the particles that have been collected on the filter.

A method is therefore disclosed for determining a mass of dust and identifying at least one component of the collected dust. The dust is drawn into a monitor containing a mass determination device that collects the dust on a filter. The monitor inlet and housing define an airflow pathway leading from an external environment into the monitor and through the filter. The filter itself consists essentially of material that is ashable for an instrumental analysis, for example a photometric analysis such as a spectroscopic analysis, without interference with one or more analytes on the filter. For example, the filter is made entirely of organic materials that are capable of being thermally or chemically destroyed for spectroscopic analysis, and that do not produce overlap or interference with the spectroscopic characteristics of the analyte(s). In particular examples, thermal or chemical destruction can take the form of thermal ashing, microwave ashing, low temperature ashing, or chemical destruction.

In the disclosed method, dust particles of a desired size range are collected from air that moves along the airflow pathway and through the filter. The mass determination device then determines the mass of dust collected on the filter, for example providing real-time nearly instantaneous readings of concentrations of dust detected in the filtered air. The filter is then removed from the monitor and ashed for spectroscopic analysis to identify the at least one component of the dust. In particular examples of the method the identified component is quartz, and in other particular examples a spectroscopic method provides a quantitative analysis that both identifies the presence of the particle and quantitates the amount of the particle that is present.

The monitor may be designed to be of portable configuration so that it may be readily moved, carried, or attached to a person working in an environment in which dust concentration is to be monitored. For example, it may be used for varied environmental sampling purposes at locations where it has been positioned, or as another example it may be attached at belt level or to the belt of a coal miner in a mine. To help assure that particulates are collected from a zone of inhalable air, a flexible conduit can be positioned to provide an air inlet opening that is located above the waist or shoulders of a person wearing the monitor, for example within 18 inches (46 cm) of the mouth and nose. Although the air inlet can be positioned on the upper chest or shoulders, it is often less intrusive to the wearer when secured to a headlamp on a helmet (hard hat) worn by the worker.

In a particular disclosed embodiment, the mass determining device is a resonance frequency microbalance (such as a TEOM® device) within the monitor that oscillates the filter at a resonance frequency that changes in response to increased mass collected by the filter. Mass determination is performed by quantitating a change in the resonance frequency of the oscillations, and this mass determination can be used to calculate a concentration of particles present in the air drawn through the filter. In the disclosed microbalance, the filter is mounted on a platform that oscillates, moving the filter and platform together. The mounting platform and filter can be removed as a unit from the monitor to minimize disturbing the particulates on the filter as may occur when the filter is separated from the mounting platform.

Particular examples of the filter are fibrous nonwoven filters that consist essentially of purely organic polymer, for example a single organic polymer, that minimizes spectroscopic signals that would otherwise be obtained if a more complex chemical composition involving inorganics was chosen. The mounting platform on which the filter is mounted is also ideally made entirely of a purely organic material, without the presence of inorganic pigments that can interfere with spectroscopic analysis. The use of an entirely organic material more readily permits ashing of the filter and its platform at a low temperature. Examples of the filter material include polyvinyl chloride, polyvinyl chloride/acrylic copolymer, polypropylene, polyethylene, polyester, or nylon. Although the filter is readily made of a single one of these materials, combinations of filter materials are also possible. The filter and its mounting support are also preferably substantially free (or completely free) of glass, polytetrafluoroethylene (PTFE), titanium dioxide, or other mineral matter. These materials, which are typically incorporated into microbalance filters, are not readily subjected to thermal or chemical destruction, and/or interfere with spectroscopic detection of analytes such as quartz. (Quartz fiber is utilized in some specialty disc filters where heat resistance is advantageous. This filter composition would also be among those unsuitable for the disclosed method.)

In a particular example of the method, the filter is subjected to infrared spectroscopic analysis, or other spectroscopic method (such as a quantitative spectrometric analysis) that determines the quantity of an analyte (such as quartz) that is present on the filter. It is often helpful for the filter to be removed from the monitor as a unit with the filter mounting platform and both the filter and platform subjected to thermal or chemical destruction such as ashing. This approach minimizes dislodgement of particles from the filter that occurs when the filter is separated from the mounting platform and minimizes handling time and effort. A support that is entirely or almost entirely of organic composition that is substantially ashable for spectroscopic analysis helps avoid spectroscopic interference between the chemical spectra of the analyte and the filter support platform material. Alternate filter assembly designs may permit the quantitative removal of the filtration element and collected dust from the assembly and the processing of the filtration element alone.

It is useful to heat air in the airflow pathway of the monitor to reduce the relative humidity of the air and avoid inaccurate mass readings that also include water deposited on or absorbed by the filter. An additional or alternative approach to this problem is to sense a relative humidity in the airflow pathway, and correct the mass determination to compensate for the moisture from the air that collects on the filter. This humidity correction approach is particularly helpful when using the organic ashable filters disclosed herein which are more hygroscopic than the highly hydrophobic filter materials used in the prior art. The humidity correction helps compensate for the use of the more hygroscopic materials that are more readily subjected to thermal and chemical destruction than the Teflon® and glass filters previously used in microbalance technology. A variety of humidity correction approaches can be used, but a particular disclosed embodiment corrects the calculated mass determination by subtracting a humidity correction factor that is proportional to change in detected airflow (or alternately ambient) relative humidity.

Because the spectroscopic analysis is often performed remotely from the dust collection and mass determination in the monitor, the removed filter (and optionally its associated mounting platform) is placed in a substantially dust-tight receptacle. In particular examples the receptacle is an ashable container, and the filter and container are ashed together. The simultaneous thermal destruction of both the container and filter (and optionally any associated mounting platform) improves the accuracy of the spectroscopic analysis by avoiding the introduction of impurities or the loss of analyte. It is often desirable that the ashable container have a mass not exceeding approximately one gram, (though lower mass may be helpful), to minimize interference with spectroscopic analysis and reduce ashing time (which may depend on ashing method, ashing equipment, and specific material ashed). In particular embodiments, the receptacle is a sealable polymeric/plastic bag, and the bag is sealed after the filter is placed in the bag for transport to a site of spectroscopic analysis.

Alternatively, the receptacle is a rigid rinsable container not intended for simultaneous thermal destruction with the filter or its associated mounting platform. In this embodiment, the filter (and any mounting platform) is removed from the container and the container is rinsed prior to spectroscopic analysis of the filter to remove any dust retained in the container so that it will be included in the spectroscopic analysis. The rigid rinsable container may be, for example, a plastic cup having a mounting device to which the filter is attached within the housing, keeping the filter immobile.

The monitor of the disclosed method determines a volume of air drawn through the filter while dust particles are collected on it, and calculates a concentration of dust in the environment from a mass of dust collected in a volume of air that has flowed through the filter. The concentration of analyte may also be calculated once the collected mass of analyte on the filter has been determined.

In addition to the disclosed method, this specification also describes a personal dust monitor that includes a housing and a mass determination device within the housing that collects dust on a filter to determine a mass of dust collected by the filter. The housing defines an airflow pathway into the housing and through the filter. Air is drawn through the airflow pathway and filter with a pump that generates a negative pressure across the filter. The filter consists essentially of organic material that is readily thermally destroyed (for example by ashing) for instrumental (such as a photometric, for example spectroscopic) analysis without interference with an analyte on the filter. For many health-related assessments, the monitor preferably includes an intake device (such as a differential particle size cyclone preseparator) that removes nonrespirable larger particles from the airflow pathway prior to them reaching the filter. An impactor preseparator may be used in other cases. The filter therefore collects particulates of a desired size range from the air that moves along the pathway through the filter.

The disclosed mass determination device in the housing is capable of nearly instantaneous and continuous determination of mass collected on the filter. The device is, for example, a resonance frequency microbalance in which the microbalance oscillates the filter at a resonance frequency that changes (for example decreases) in response to increased mass on the filter. In a particular example, the microbalance is a tapered element oscillating microbalance, for example a TEOM® personal dust monitor.

As already noted, the filter can consist essentially of a single polymer or combination of polymers (such as polyvinyl chloride, polyvinyl chloride/acrylic copolymer, polypropylene, polyethylene, polyester, or nylon), and is substantially or completely free of glass, quartz fiber, polytetrafluoroethylene (PTFE) or titanium dioxide. The filter is a nonwoven material that can contain a fiber binder in addition to the organic fibers of the filter. In some embodiments, the filter fibers may be self-binding. The filter can also include a backing, particularly a backing made of a nonhygroscopic material, for example a thermoplastic or a noncellulose material.

Within the monitor, the filter is mounted to a support that oscillates in a unit assembly with the filter and is removable from the instrument housing. The support also consists essentially or entirely of organic material that is ashable for spectroscopic analysis without spectroscopic interference with an analyte on the filter.

The monitor may also include a connector for connecting the housing to a person wearing the personal dust monitor, for example a belt attachment that allows the monitor to be secured to the belt of a coal mine worker. An elongated flexible conduit attached to the monitor also provides an air inlet with a mount for mounting the air inlet on the upper body (for example on the shoulders or head) of a subject wearing the personal dust monitor. The monitor may also include one or more heaters for the airflow pathway to help heat the air and reduce its relative humidity, a humidity sensor that senses humidity of air in the airflow pathway, and a humidity compensator that corrects the determined mass of dust to compensate for an effect of humidity on mass determination via filter moisture absorption characteristics. The monitor may also be present in a kit that contains the substantially dust-tight receptacle for transporting the filter once the filter is removed from the housing. The kit may also include multiple interchangeable TEOM units of different designs to accommodate use of different filter types.

In some embodiments, the monitor is present in a kit that includes attachable heat-resistant inlets, for example steel or glass tubes, which may be mounted at the end of or replace the flexible inlet conduit. An attached inlet is then placed in a particulate-bearing gas effluent stream, for example an industrial exhaust stack or an engine tail pipe. The diameter of the inlet and the air sampling rate are selected to achieve an isokinetic sampling arrangement in which no particle concentration or size bias occurs from the sampling process. An industrial dust sample is thereby collected which is subsequently analyzed for one or more analytes after ashing of the TEOM filter.

The foregoing and other features and advantages of the invention will become more apparent from the following detailed description of several embodiments which proceeds with reference to the accompanying figures.

BRIEF DESCRIPTION OF THE FIGURES

FIG. 4 is an enlarged view partially in cross-section of the microbalance component of the personal dust monitor of FIG. 1.

FIG. 5 is a side view partially in cross-section of a dust-tight container for transporting the filter and its mounting platform. The removable lid of the container has been removed to place the filter and mounting platform assembly in the container.

FIG. 6 is a view similar to FIG. 5, but showing the filter and mounting platform placed within the container on which the lid has been placed.

FIG. 7 is a view of dust tight bag into which the filter and its mounting platform can be placed for transportation. The bag can be sealed by an adhesive strip on the bag that is selectively exposed by removing a protective barrier from the adhesive.

FIG. 8 is a view of another embodiment of a dust-tight bag which is selectively sealed with a mechanical closure member.

DETAILED DESCRIPTION OF SEVERAL EMBODIMENTS

Abbreviations

FTIR: Fourier Transform Infrared Spectrometer
IPA: Isopropyl Alcohol
LTA: Low Temperature Asher
PDM: Personal Dust Monitor
PP: Polypropylene
PVC: Polyvinyl Chloride
PVCA: Polyvinyl Chloride/Acrylic Copolymer
RH: Relative Humidity
TEOM: Tapered Element Oscillating Microbalance

Terms

An instrumental analysis refers to an analysis performed with a scientific instrument, for example an automated spectroscope. An analytical instrument detects and/or quantitates a signal originating with a physical or chemical property of a sample, typically changing it from a form not directly detectable or measurable by an analyst into a form that can be detected and measured.

A photometric analysis involves an analytical procedure or physical phenomenon in which light energy originates from or interacts with a sample. This may involve light emission, absorption, scattering, refraction, diffraction, or rotation. Spectrometry of electromagnetic energy (spectroscopy) in its many forms characterizes this class of analysis.

A nonphotometric analysis involves an analytical procedure or physical phenomenon other than generation or interaction with light. This may involve measurement of mass, electrical properties, thermal properties, particle-type radioactivity, or other exploitable sample characteristics. For example, mass spectrometry characterizes mass-to-charge ratio, coulometry measures electrical current, and some particle counters only record electrical pulses.

Spectroscopic interference involves the overlap of analyte signal bands by signal bands of nonanalyte materials in the sample.

Interference in the general sense, for example in nonphotometric analysis, involves any impairment in analyte signal strength, quality, or accuracy caused by nonanalyte materials in the sample.

Personal Dust Monitor

A method and device are disclosed that allow a monitor to sample air in the breathing space of a subject, quantitate an amount or concentration of ambient particulates such as dust, as well as identify and/or quantitate a particular component of the particulates.

Figure 1:
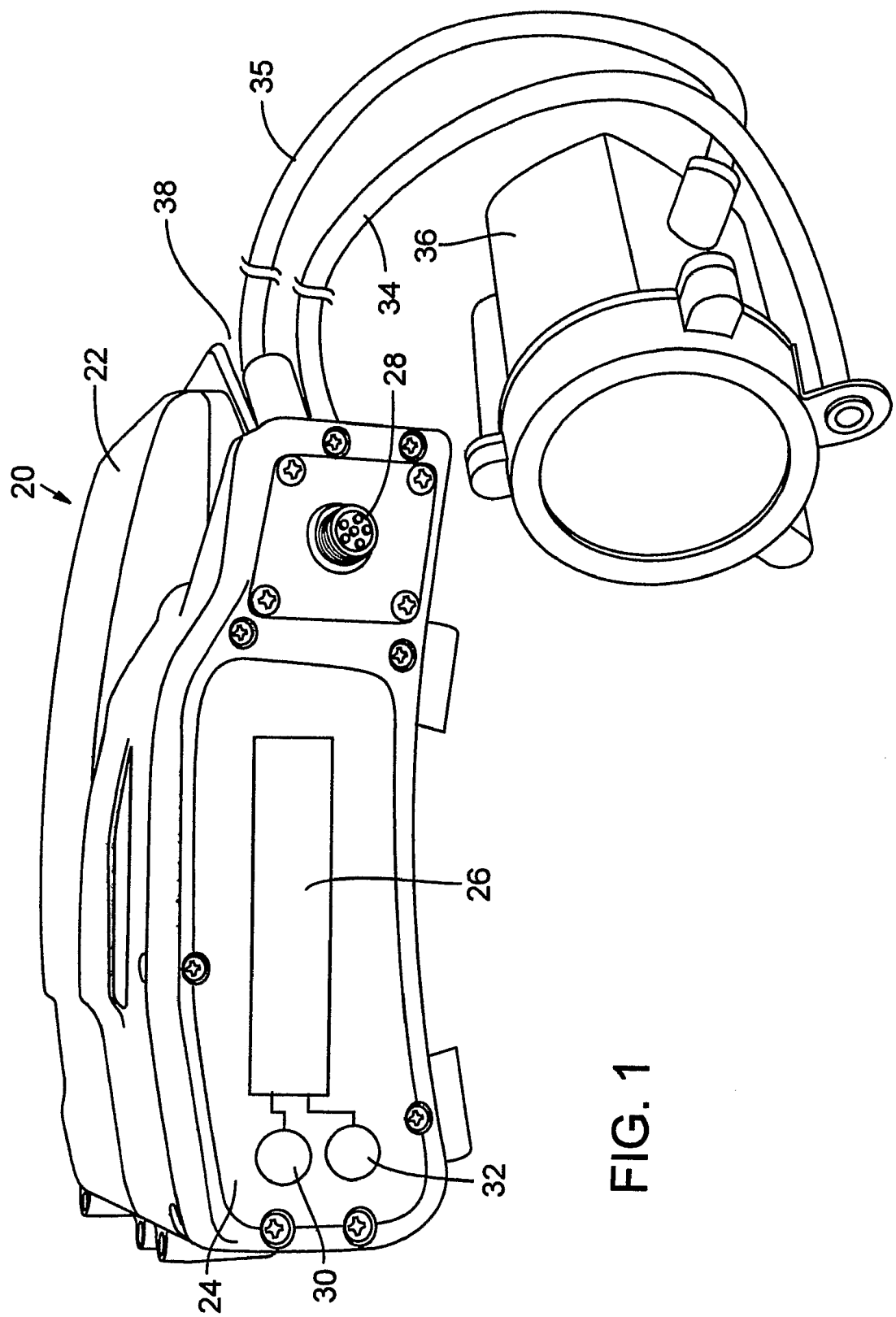
FIG. 1 is a front view of a disclosed embodiment of the personal dust monitor and flexible conduit that attaches the monitor air inlet to a head lamp for mounting on a helmet.
Figure 2:
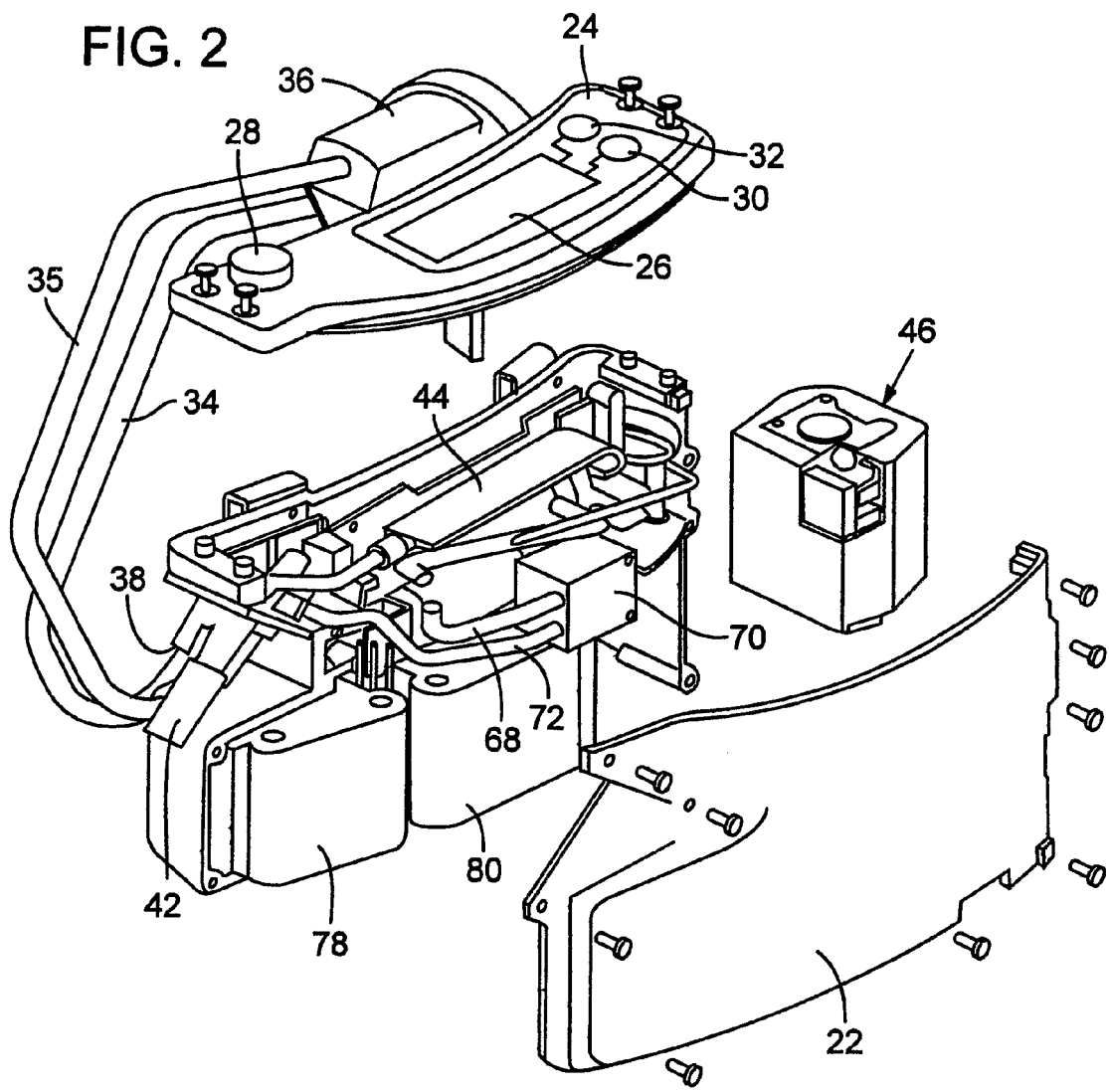
FIG. 2 is an exploded schematic view of the personal dust monitor of FIG. 1.
Figure 3:
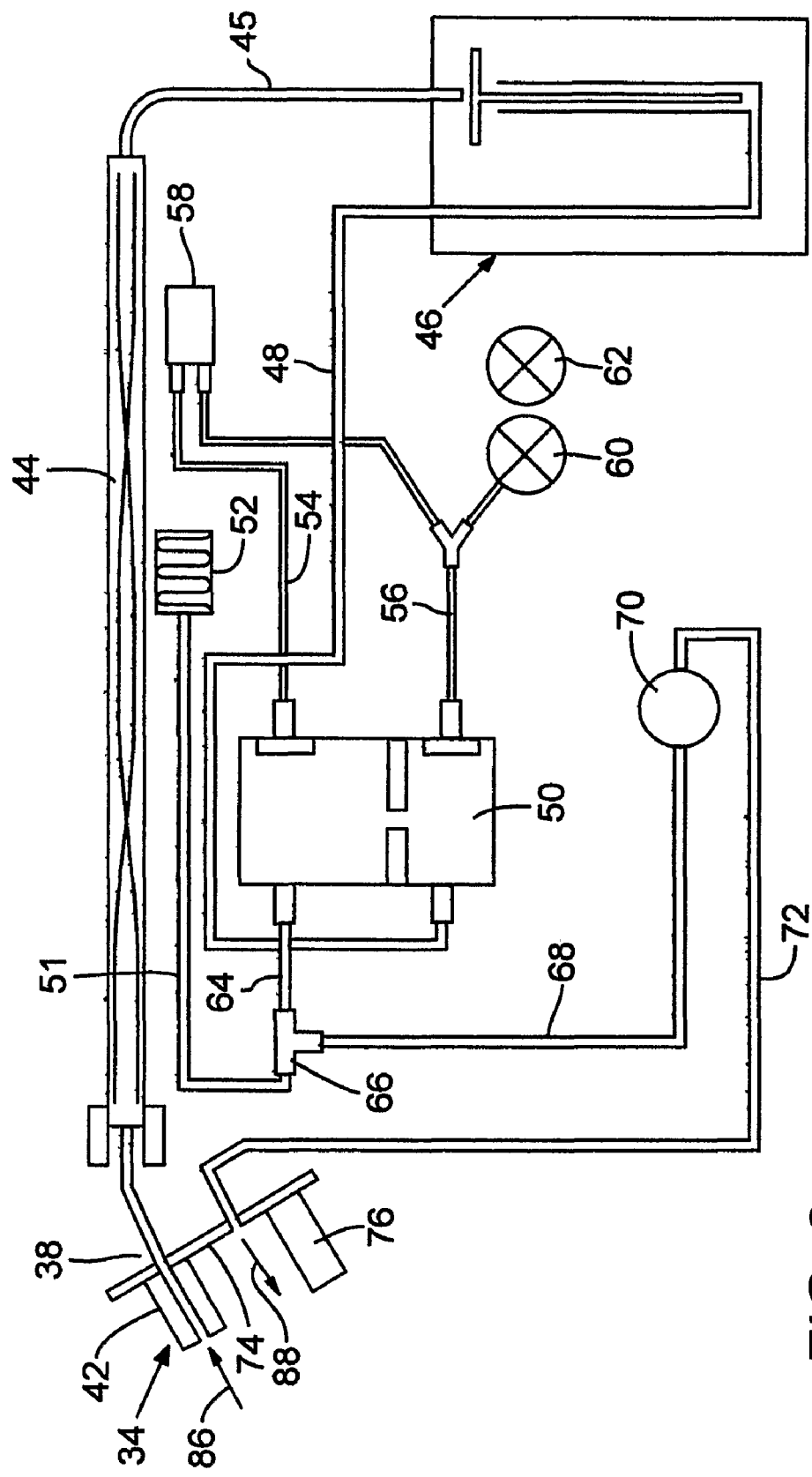
FIG. 3 is a schematic view of the personal dust monitor of FIG. 1.

The disclosed method can be performed with a device such as the TEOM® series 3600 Personal Dust Monitor shown in FIG. 1, wherein a personal dust monitor (PDM) 20 is contained within a housing 22 having a front face plate 24 that includes a display screen 26 which displays operational information and output from monitor 20. A cable port 28 is also located beside the face plate 24 for connecting monitor 20 to an external power source, such as may be available via mining machinery. A flexible depressible activation switch 30 and scroll switch 32 are also visible on face plate 24. A hose line 34 provides a flexible tube that connects cap lamp 36 with an air inlet 38 (FIGS. 1-3). Hose 34 is a conductive silicone rubber tube of 0.48-cm internal diameter and 152-cm length that is capable of conveying particulate-laden air through it at 2.2 L/min. A power line 35 carries electrical energy to cap lamp 36 from PDM 20. Lines 34, 35 are of sufficient length to comfortably extend between the housing 22 to cap lamp 36 when the PDM housing is worn at a belt-level location on a user. Lines 34, 35 are typically closely bound together within a durable synthetic fabric sleeve (not shown) to make them more manageable and comfortable for the worker wearing the monitor.

The internal design of monitor 20 is illustrated in FIGS. 2 and 3, which show that air inlet 38 communicates with the remainder of an airflow pathway through an externally-mounted Higgins-Dewell (HD) type cyclone differential particulate separator 42 that leads to a heated airflow conduit 44 that allows heated air to flow into a removable TEOM microbalance 46 that is described in greater detail below in connection with FIG. 4. As illustrated in FIG. 3, the airflow pathway continues through conduit line 48 that leads to an air sensor and relative humidity sensor block 50 that communicates through line 51 with a pulsation dampener 52. Lines 54, 56 provide a fluid circuit in which are included flow differential pressure sensor 58, filter loading pressure sensor 60, and ambient pressure sensor 62. Line 64 merges with line 51 at T-junction 66 to join pump line 68 that communicates with a pump 70 and outflow line 72 that communicates with an external housing outlet port 74. An ambient temperature sensor 76 is positioned adjacent outlet port 74.

As illustrated in FIG. 2, a rechargeable cap lamp battery 78 is positioned within PDM 20, and provides direct current through power line 35 (FIGS. 1 and 2) to cap lamp 36. A rechargeable PDM battery 80 (FIG. 2) is provided adjacent battery 78, and it provides direct current for the operation of the PDM itself, and for internal electronic circuitry (including a programmable memory) that is not shown in the drawings. In the disclosed embodiment, the PDM is operated with a Windows®-based computer interface software.

In manual mode of operation, PDM 20 is activated and controlled with switches 30 and 32. Electrical energy from battery 80 activates and powers the components of PDM 20. Activated pump 70 draws in ambient air as indicated at arrow 86 (FIG. 3) from hose line 34 through cyclone separator 42, where dust is separated into coarse and respirable fractions. When operated at a flow rate of 2.2 L/min, the coarse dust remains in the dust pot of cyclone separator 42 while a respirable fraction of particulates in the air continues into the analytical portion of the unit.

After this separation step, the air moves through heated conduit 44 where the air is heated to a constant temperature, typically about 45° C., in an elliptical cross-section metal tube designed for low particulate loss. Air is drawn through an air line 45 into TEOM 46 to deposit any ambient dust on a filter in the microbalance (as discussed further in connection with FIG. 4) where the weight of the collected dust is continuously determined by the inertial microbalance. Dust concentration is subsequently displayed on screen 26. As air continues through the fluid circuit of PDM 20, the air temperature and relative humidity is sensed at sensor block 50, pulsations are dampened at pulsation dampener 52, and flow differential pressure is sensed at sensor 58 before the air is expelled from the circuit at outlet port 74. The temperature of ambient air is sensed at 76 near outlet port 74, where air is expelled as indicated by arrow 88.

The PDM 20 is further described in Patashnick et al., Tapered Element Microbalance Technology in DeSouza E., ed. Mine Ventilation: Proceedings of the North American/Ninth U.S. Mine Ventilation Symposium (Kingston, Ontario, Canada, Jun. 8-12, 2002), as well as in Volkwein et al., Performance of a New Personal Respirable Dust Monitor for Mine Use, DHHS (NIOSH) Pub. No. 2004-151, RI 9663 (also available in PDF format on the internet from the National Institute for Occupational Safety and Health).

Custom software may be used to program PDM 20 through a personal computer. In particular embodiments, a mass of total dust on the TEOM filter is determined by internal electronics, and concentrations based on flow rate and time are calculated and displayed on display screen 26. Dust mass and concentration data and other operational parameters (such as flow rate, filter differential pressure, tilt status, shock status, temperature, relative humidity, and TEOM frequency data) are simultaneously recorded to internal memory for later analysis.

PDM 20 may be operated in programmed or manual modes. The programmed mode may be initiated through a personal computer software interface to start measurements at a specific time and run throughout a specified duration of a shift. At the end of the program shift time, the unit retains the final exposure data in the screen display until the memory of the monitor is downloaded to a personal computer. Several shifts of data may be retained in the PDM's internal 2-megabyte memory.

Microbalance

PDM 20 contains a removable inertial microbalance 46, which in the disclosed embodiment is a Tapered Element Oscillating Microbalance (TEOM®). TEOMs are known, and their structure and function is described, for example, in U.S. Pat. Nos. 3,926,271; 4,391,338; 6,016,688; 6,080,939 and 6,465,749. Although the structure of TEOMs is known, an example is briefly described herein. As shown schematically in FIGS. 2 and 3, and illustrated in greater detail in FIG. 4, a TEOM housing 100 contains a sampling airflow inlet 102 through which sampling air 104 is drawn in from line 45 (FIG. 3) with which TEOM 46 communicates. Inlet 102 communicates with a bell-shaped inlet chamber 106 having a filter assembly 108 in a recessed microbalance oscillation chamber 109 at the bottom of chamber 106. Filter assembly 108 includes a filter 110 mounted on a circular polypropylene base 112 with a hollow axial stem 114, which in turn is mounted on a free end of a tubular microbalance element 116. Tubular element 116 may be tapered or nearly cylindrical, but it is preferably fabricated with a thin wall thickness to increase sensitivity of the microbalance. Tubular element 116 is mounted near its fixed end to a base 118 through which the hollow open end of element 116 extends. An electronic control circuit senses its vibration and through positive feedback adds sufficient energy to the system to overcome losses. For example, electromagnetic drivers 122a, 122b are mounted in opposition to one another on either side of element 116, to which is fixed two small magnets 124a, 124b that interact with drivers 122a, 122b to maintain a desired oscillation frequency of element 116. Several electromagnetic drive arrangements are disclosed, for example, in U.S. Pat. No. 3,962,271.

The PDM filter assembly 108 (FIG. 4) that is used in the Rupprecht & Patashnick PDM is constructed from three sonically-welded components. The largest component is circular polypropylene support base 112 with its hollow axial stem 114, which frictionally attaches to the exposed end of tubular element 116. The second component is small circular fibrous filter mat 110 which mounts on base 112, and the final component is a polypropylene ring used to seal the rim of the filter onto the base. The filter assembly may be mounted and removed from element 116 using a special tool (not shown). The mat 110 is made from Teflon® and fiberglass to provide a hydrophobic surface with inherently low hygroscopicity. Filter assembly 108 is also shown in FIGS. 5-8 and 13-15 and described below in relation to its handling with disclosed containers for it and also its own characteristics.

In operation, PDM 20 is activated so that a fixed resonant oscillation of microbalance element 116 is achieved. Air is drawn through PDM 20 by the operation of pump 70 (FIG. 3) such that inlet air 104 (FIG. 4) is drawn through inlet 102 and chamber 106, through filter assembly 108, tubular element 116, and out of the open fixed end of the tubular element as indicated by outlet air 126. The air then moves through line 48 (FIG. 3).

As particles drawn along the airflow pathway become entrapped on filter 110, the mass being oscillated increases and the resonant frequency of oscillation changes. A precise electronic counter measures the frequency, and calculates its relationship to changing mass. The mass of the entrapped particles is therefore determined by measuring changes in the resonant frequency of oscillation of member 116. Further details about this technique are described in U.S. Pat. No. 4,391,338.

Although microbalance 46 can determine a mass of particles trapped on the filter 110, it can not determine the chemical identity of the deposited particles. Hence it would not be known if the particles were coal dust, quartz, or a combination thereof. Moreover, it is not possible to determine from the output of the device whether quartz or any other specific trapped particulate is present in amounts that could be harmful to human health.

Example 1

Spectrometry

Spectroscopy or spectrometry is the science of recording the spectra and measuring the absorption or emission of different wavelengths of visible or nonvisible light for materials of interest. This can be done via a spectrometer, which may contain slits, prisms, gratings, collimating and object lenses, mirrors, interferometers, light sources, light detectors, or a variety of other components appropriate for the method involved. Absorbance spectroscopy involves exposing a sample to a source of light and determining what portion of the light intensity emerges from the sample, with the remainder being absorbed. Reflectance spectroscopy is a variation in which the reflected intensity of light is measured. Emission spectroscopy involves obtaining spectral information by exciting a sample to be analyzed to spectroemissive levels. Material samples may be simple or complex, containing only one or many analytes of interest. Qualitative spectroscopy generally seeks to detect or identify a material in a sample. Quantitative spectroscopy is a spectrometric technique that builds on the qualitative identification and produces information about a quantity of an analyte present in a sample.

Many variations in spectrometric approach can be used in association with the methods disclosed in this specification, the generalities of spectroscopy having some pertinence. A spectroanalytical instrument may measure only one spectral line, band, or frequency, or it may simultaneously measure numerous bands or lines. In general, it is desirable to concurrently measure multiple bands or lines, or full spectra of some portion or range in the wavelength continuum, expanding the amount of data gathered with each experiment or analysis. Associated background measurements or spectra are typically collected, as reference measurements for the sample. It is desirable that spectra, both for the sample and reference measurements avoid unnecessary complexity, particularly the overlap of spectral characteristics from nonanalyte materials with those of the analyte. Correction procedures for such interferences may be imperfect and can still leave the analyte measurement accuracy impaired. It is therefore sometimes a useful practice to ash or digest samples by a thermal or chemical process, to simplify their makeup and their resultant spectral properties. It also serves in recovering more analyte for the analysis than achieved by more limited sample dissolution, leaching, or suspension methods. Many different spectroanalytical techniques have been developed which the disclosed device and methods can employ. Some specific examples of such different types of spectrometry include:

Infrared Spectroscopy IR)—an analytical technique which measures at wavelengths (or frequencies) in the infrared spectral region (near-, mid-, or far-IR) that are absorbed or reflected by a specimen, characteristic of its molecular constitution. Infrared absorption bands identify organic molecular structure components or functional groups (aromatic, aliphatic, ketone, alcohol, amine, etc.) and are also useful in identifying inorganic materials, such as minerals. The frequency at which absorption occurs reflects the frequency at which bonds in these materials stretch and/or bend.

Raman Spectroscopy—a technique that is complimentary to IR, in which a sample is exposed to intense monochromatic light. The wavelength and intensity of the resultant scattered light is measured. The low-intensity scattered light occurs at wavelengths shifted from that of the incident light corresponding to the energies of molecular vibrations of materials in the sample.

Ultraviolet-Visible Spectroscopy (UV-Vis)—an analytical technique which measures a range of wavelengths (or frequencies) in the ultraviolet and visible regions of the electromagnetic spectrum that are absorbed by a specimen, which characterize the electronic energy levels of its molecular constituents. UV-Vis absorption bands may be characteristic of certain molecular components, such as aromatic or carbonyl groups. Minerals and metallic complexes may also have characteristic bands.

Mass Spectrometry (MS)—a chemical analysis technique in which the substance to be analyzed is placed in a vacuum and reduced to low pressure. The resulting vapor is exposed, for example, to a beam of electrons which causes ionization to occur, either of the molecules or their fragments. The ions thus produced are accelerated and then passed through a mass analyzer that separates the ions according to their mass. MS is not a photometric method. Instead it produces and records a mass spectrum of charged molecular fragments. Among the uses of the technique is the detection and measurement of metal ions and metal-based compounds.

Atomic Absorption (AA), Inductively Coupled Plasma (ICP), and X-Ray Fluorescence (XRF) Spectroscopies—These three methods are very useful for analyzing metals. It is common for variations of these methods to require thermal or chemical destruction of an organic sample matrix, for example destruction of an air filter on which particulate matter has been collected, before analysis. These methods are frequently described in texts on instrumental analytical methods and spectroscopy.

X-Ray Diffraction Spectroscopy (XRD)—This is the crystallographic method of choice in working with minerals. Some variations of this method require thermal or chemical destruction of an organic sample matrix, for example destruction of an air filter on which particulate matter has been collected, before analysis. This method is frequently described in texts on instrumental analysis and mineralogy.

Fluorescence Spectroscopy—an analytical technique which measures a range of wavelengths (or frequencies) of light a molecule emits in passing from a higher to lower energy state during a given time period (such as the first millisecond) after absorbing a photon of light. Fluorescence wavelengths and emission intensity reflect the redistribution of energy in the molecule after light absorption. Fluorescence excitation spectroscopy reflects the efficiency with which a molecule converts absorbed energy into fluorescent emission as a function of the wavelength of the absorbed photons.

Phosphorescence Spectroscopy—an analytical technique which measures a range of wavelengths (or frequencies) of light a molecule emits in passing from a higher to lower energy state on a time scale beyond the first millisecond after absorbing a photon of light. Phosphorescence wavelengths and emission intensity also reflect the redistribution of energy in the molecule after light absorption. Phosphorescence excitation spectra reflect the efficiency with which a molecule converts absorbed energy into phosphorescent emission as a function of the wavelength of the absorbed photons.

Depending on the type of analytes involved, the preferences of the analyst, and the variations in sample preparation employed, forms of spectrometry other than those discussed above might also be used with the disclosed monitor and methods. Nonspectrometric methods might also be employed in some cases, such as coulometric determination or radioassay of an analyte subsequent to the ashing of a TEOM filter. Metals and radioactive elements would be example analytes for these approaches, respectively. The absence of unashable or interfering materials in filter assembly components would be advantageous not only for spectrometric methods, but for the full range of alternate analytical methods as well.

Example 2

Filters for Determination of Quartz in Collected Dust

Quartz analysis of coal mine dust has been performed in the past by collecting samples on 37-mm-diameter 5.0-μm-pore polyvinylchloride (PVC) membrane filters, using standard cassettes designed for air sampling in mines. The Mine Safety and Health Administration employs its P-7 method of analysis, which involves low-temperature ashing of the PVC sample filters (for example at 250-500° C.) and redepositing the ash onto PVC-Acrylic (PVCA) membrane filters, by means of an isopropyl alcohol (IPA) suspension. The redeposited samples are then examined in a Fourier transform infrared (FTIR) spectrometer. Through appropriate calibration procedures, the FTIR output is used to quantify the mass of quartz in the samples. The method includes a correction for kaolin clay, a common mineral interferent that may be found in coal dust samples.

Existing TEOM and PDM filters are inherently different from PVC membranes in regard to structure, composition, and mass. For example, the filter material used by Rupprecht & Pataschnick for its commercial 1400-series TEOM instrument is EMFAB TX40H120WW, a product of Pallflex Products Corp. (Putnam, Conn.; a division of Pall Gelman Sciences). This high efficiency filter contains three particularly rugged materials. The filter medium is a mat of random borosilicate glass fiber, with a polytetrafluoroethylene (PTFE) polymer binder cured at over 370° C. A layer of woven glass fabric is also incorporated as a backing, for structural reinforcement. Although sample ashing is used as a means of eliminating spectral interferences from the organic portion of samples, the existing PDM filter is substantially unashable. The resistance of the filter to thermal destruction is particularly problematic with a low temperature asher (LTA), which is the usual means of filter and organic dust destruction in quartz analysis of coal samples.

Additionally, on-filter analysis is problematic because it is difficult to cut the filter cleanly from the polypropylene components holding it. Also, because the fibrous filter is very thick and opaque in comparison to membranes, it transmits insufficient infrared light for successful on-filter analysis, and scatters much of the infrared light it does not absorb. The polypropylene components of the PDM filter are also a problem because their mass is much greater than that of a membrane filter. The masses of ring/base pairs usually range from about 90 to 100 mg (105-115 mg including a filter mat). This is many times greater than the mass of the PVC filter itself, which typically ranges about 12-15 mg. The large mass of nonfilter portions of the filter assembly would necessitate long ashing times, and fillers and additives that are typically a portion of each polymer formulation would also frustrate accurate spectrometric analysis.

For example, white colored polypropylene components are tinted with 0.5 percent titanium dioxide ($TiO_2$) pigment and also contain other inorganic materials such as polymer additives, antioxidants and pH neutralizers. Because P-7 analysis has a declared limit of quantitation (LOQ) of 20 μg quartz, interference from these other higher-mass inorganic materials is unacceptable.

The filter itself is typically of nonshedding fibrous construction that maintains a very high dust retention capacity that is capable of collecting several milligrams of mine dust on a 14-mm diameter filter. In addition to filtering efficiency, the filter avoids excessive pressure drop. Filter assemblies 108 that met these criteria were fabricated having compositions as close to 100 percent organic as possible. The new filters were then tested in actual quartz determinations to demonstrate that they were suitable as replacements for the existing filters.

Initial Ashing and Dispersion Tests

A number of polypropylene components for PDM filters were ashed in a low temperature asher (LTA) to demonstrate that they could be ashed within a reasonable period of time and that the residue readily dispersed in IPA. These are the highest mass items that are incorporated into a PDM filter assembly, and are therefore the most difficult to ash. Settings for the asher were those typical for ashing membrane filters. The samples were removed at 30-minute intervals and weighed to track mass loss with progressively longer ashing times.

Residue of the samples had a stable visual appearance after about 5.5 hours of ashing, and there was no significant additional mass loss after 6.5-7 hours. In that approximately 7 hours were adequate to ash PDM samples, it was demonstrated that PDM samples can be practically ashed within a single work day. (Longer ashing times were used in later tests, simply to completely guarantee sample destruction with the ashing devices available.) Of course, ashing times could be shortened by using more aggressive procedures, but the settings used were consistent with maintaining the useful lifespan of the ashing device. In particular low temperature ashing that avoids modification or destruction of quartz as an analyte, the ashing temperature is no more than about 500° C., for example no more than about 250° C.

White polypropylene components left much more visible ash than clear components. However, both types of ash dispersed in IPA with only a very brief period in an ultrasonic bath. The ash was a very fine powder that left no polymer to act as a binder, which demonstrated that the P-7 procedure was successfully applied to PDM filter assemblies.

In contrast, a polytetrafluoroethylene (PTFE) filter could not be ashed under these conditions. PTFE and Reemay™ polyester were considered because of their presumed hydrophobicity, which would minimize deposition of ambient moisture on the filter. A 25-mm diameter, 1-2 μm-pore, PTFE filter (catalogue no. 12009-M-1132, Berghof/America, Concord, Calif.) was cut into smaller pieces and weighed. The pieces were subjected to extended times in an LTA and mass loss determined at different times. At the measured ashing rate, approximately two continuous weeks of ashing would be needed for full filter destruction, which is an impractical period of time for large scale analyses. Although PTFE is regarded as highly hydrophobic, PTFE components were found to be unsuitable for this filter design because of the tendency to require highly extended ashing times. (Of those polymers that have fluorine in their molecular structure, only partially fluorinated polymers may be regarded as candidate materials. They would have hydrophobic properties similar to PTFE, but by virtue of not being fully fluorinated may be ashed with less difficulty.)

Reemay™ polyester filter material (BBA Group, Nashville, Tenn.) was also eliminated from further study. This polyester product line had an undesirably low filtration efficiency (although creation of a high efficiency filtration product is a current and ongoing project of the manufacturer). Polyester is not unique in its general properties and will absorb some amount of moisture. Polyester may be regarded as more hydrophobic than nylon, but not as hydrophobic as polyethylene, polypropylene, and certainly not PTFE and related materials. Subtle variations in composition and treatment may also make a difference in many properties, moisture resistance among them. The polyester product would reside on a relative scale of mechanical, thermal, and chemical properties not unique from other polymeric materials. Therefore, it is the application of the criteria, methods, and principals of this research that enable the adoption of many polymers into useful analytically-compatible filters (reduce their use into practice), rather than the unique properties of the polymers themselves.

Spectrometric Evaluation of Filter Materials

Candidate filter materials listed in Table I were ashed to illustrate which filter materials satisfy the criteria previously discussed. Squares of the candidate filter materials were cut out (about 12-13 mm on each side) to approximate the area of the PDM filter. Because PP filter components had spectroscopic properties as unknown as the candidate filters, samples of them were also included in these tests. PVC and PVCA membranes, filters currently used in the P-7 method, were included for comparison as reference materials. All samples were ashed in an LTA for a total of 16 hours; then samples were dispersed in isopropyl alcohol (IPA), redeposited on to PVCA filters, and subjected to Fourier transform infrared (FTIR) spectrometer examination using a Perkin Elmer Spectrum 2000 FTIR spectrometer with version 2.00 Spectrum software. Most samples left minimal residue after ashing and all dispersed readily in IPA following brief sonication. Minor deviations from the usual P-7 procedure were chosen for this particular set of analyses. Instead of 1 scan per sample at 8 cm$^{-1}$ (wavenumber) resolution with 1 cm$^{-1}$ data point display, 64 co-added scans were performed at 4 cm$^{-1}$ resolution with 1 cm$^{-1}$ data point display, maintaining the visual detail of each IR spectrum, but minimizing random noise levels.

Table I shows the series of outputs derived from P-7 analysis of materials from this spectroscopic analysis. Integrated absorbances around 917 and 800 cm$^{-1}$, used for quantifying kaolin and quartz, are shown. The presumed (false) masses of these two minerals, resulting from calculations with the integrated absorbances, are also given. Finally, an estimated LOQ is recorded, based on a factor of 10 multiple of the average absolute value of false quartz mass for each material tested.

The upper rows of Table I record data for PVCA and PVC filters, the comparison references. The data for these reference materials shows minimal false readings for both kaolin and quartz and LOQs of 4-6 µg. While work with coal dust field samples generally allows an LOQ of 20 µg, a 5 µg LOQ is achievable with ideal lab conditions and handling only pure quartz as the analyte, so this estimate is generally in agreement with actual experience. None of the materials tested show large false readings for kaolin, indicating that this particular factor would not be of much consequence in filter substitution. However, white PP ring/base pairs and a spun bound cover for electret filters caused substantial negative quartz readings. Both contain TiO$_2$ which acted as a spectroscopic interferent.

Figure 11:
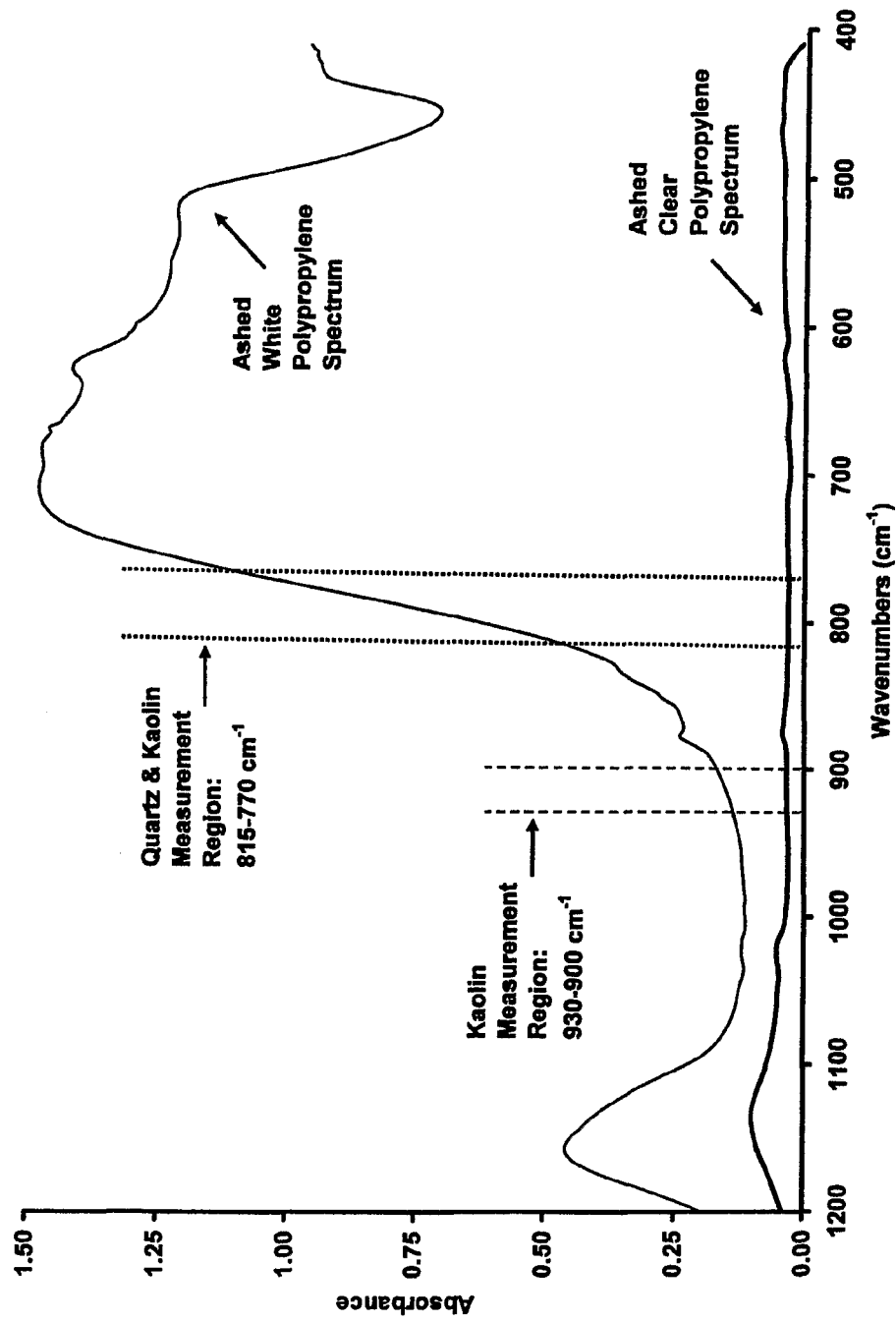
FIG. 11 is a comparison of the IR spectra of ashed white and clear polypropylene components of a filter assembly.

FIG. 11 shows IR spectrum traces of ashed white and clear polypropylene ring/base pairs that were included in this evaluation, which further illustrates how TiO$_2$ is a problem in these analyses. The ashed clear PP material produced a relatively featureless spectrum in comparison to the ashed white PP material. The white PP produced a very broad and strong peak that ranges from roughly 850 to 450 cm$^{-1}$, which was caused by the TiO$_2$ residue that could not be ashed. In the P-7 method, kaolin is measured between 930 and 900 cm$^{-1}$, which is not greatly affected by the TiO$_2$ peak. However, both kaolin and quartz are measured between 815 and 770 cm$^{-1}$, which is on the TiO$_2$ peak shoulder. When a baseline is drawn across the 815 to 770 cm$^{-1}$ region, a false negative absorbance results, from the gap between the baseline and spectrum trace curving underneath it. The curvature of the TiO$_2$ peak shoulder introduces a negative bias into the quartz measurement. Only the clear PP filter components can be successfully used for quartz analysis. Table I demonstrates that if filters are made of essentially purely organic polymeric material, and especially if TiO$_2$ is avoided, a variety of illustrated filter compositions will be suitable for spectroscopic examination after ashing, particularly if their estimated LOQ is within the desirable 20 µg practical target for field samples. A filter assembly could be made from a single essentially pure polymeric material, essentially pure copolymeric material, or a combination of multiple such materials.

Of the samples spectrometrically tested, a HEPA version of a nylon fiber filter material (manufactured by Pallflex) provided excellent results. Its filtration efficiency and pressure drop characteristics were similar to the standard fiberglass filter used in existing PDM filter assembles. Fiberglass and nylon contributions to differential pressure were essentially the same at 13-14 mm Hg, when normalized to hypothetical sample diameters of 14-mm, the actual PDM filter size. PDMs are designed to handle pressure drops up to 125 mm Hg, so both the fiberglass and nylon materials permit heavy dust samples, which produce large differential pressures, to be collected without quickly exceeding this limit.

When combined with clear PP components, the HEPA nylon's resultant estimated LOQ would be an acceptably low 8 µg quartz (5 µg from the filter plus 3 µg from the clear PP contribution). While other materials would be suitable, HEPA nylon fiber was the best existing match for the full set of desirable properties.

Example 3

Quartz Analysis with Open Face Collected Samples

This example illustrates two variations of the nylon fiber filter, one with a cellulose support backing, the other with a polyester backing (having product designations N1840 and N1841, respectively).

Prototype PDM filter assemblies were fabricated using both cellulose- and polyester-backed nylon fiber mats. Particulate collection from air suspension was chosen as the means for introducing controlled masses of quartz onto these filters for trial analyses. A direct open-face collection method was used in initial collections to avoid any complicating factors that collection through an actual PDM might introduce. Utilization of PDMs for quartz collection was reserved for a subsequent set of tests.

Two test runs were performed in a Marple chamber (EL-PRAM Systems Inc., Minneapolis, Minn.), using Minusil-5 quartz dust (U.S. Silica Company, Berkeley Springs, W. Va.). The chamber generates a dust source using a model 3400 fluidized bed aerosol generator and a model 3012 charge neutralizer, both from TSI, Inc. (St. Paul, Minn.). Cellulose-backed PDM filters and polyester-backed PDM filters were arranged in alternating order in a circle, collecting parallel samples. They were mounted on the chamber's rotating turntable to provide area-averaging of the test atmosphere. All samples were collected with Escort Elf pumps (Mine Safety Appliances, Pittsburgh, Pa.) operating at 2.2 L/min, turned on and off as simultaneously as possible. An R&P model 1400a TEOM was used to monitor each run and help collect masses of 500 µg quartz per sample. Samples were collected over either one or two hour periods, and dust feed rates into the chamber were manipulated to achieve the target collected masses in the specified time spans. Airborne Minusil-5 concentrations typically ranged from 24 mg/m$^3$. Relative humidity was maintained in the range of 40-60 percent.

All samples were pointed downward and had small aluminum foil cowls above them during sampling (Marple chamber airflow proceeded from top to bottom). This ensured that all dust mass on the filters was from air sampling and not gravity-caused settling onto nonfilter surfaces. Weighed filters were placed directly in clean glass beakers, ashed for at least 10 hours, redeposited with IPA onto PVCA filters, and subjected to spectrometric analysis. The spectrometric examination procedure of the P-7 analyses was performed twice on each ashed sample, both utilizing a reference absorbance spectrum subtracted from the absorbance spectrum of each sample. One procedure variation retained the typical subtraction of a PVCA filter spectrum, while a second variation employed subtraction of an ashed PDM filter that had been redeposited onto a PVCA filter. This comparison was used to reveal if fully matching spectral references to samples was of importance in these PDM filter analyses.

Tests were also performed to demonstrate that the Minusil-5 source of quartz dust produced an expectable P-7 mass determination 5.8 percent less than the corresponding gravimetric value. Most of this correction likely derives from the Minusil-5 being slightly lower in actual quartz content than SRM 1878A (the reference quartz material used in P-7 analysis).

Table II summarizes the results of these open-face tests. The table reports collected quartz masses, based on gravimetric assessment, and the expected P-7 results, based on a 0.942 correction factor. Actual P-7 mass assessments are also reported, for both variations of reference spectra subtracted, as well as percent deviation of P-7 results from what was expected. It can be readily seen that there is minimal difference between actual and expected P-7 mass determinations, accuracy averaging within about 1 percent. The 95 percent confidence interval for mean difference between actual and expected P-7 results is within 3 percent. The data also shows that the ashed PDM filters can be used as spectral references without making any practical difference in analytical accuracy.

Example 4

Quartz Analysis with PDM-Collected Samples

In this example, Minusil-5 was collected onto nylon fiber PDM filters while the filters were mounted in PDMs during sampling runs. Half the filters had cellulose support backings and the other half had polyester backings. The same Marple chamber and dust generating and monitoring apparatuses used for the initial air collection tests were used here as well. Each filter composition underwent 6 tests, with each test employing 3 PDMs and 4 HD cyclones operated in parallel, all drawing air at 2.2 L/min. The cyclones collected samples on 37-mm diameter PVC filters, which served as the comparison references for the PDM filters. PDM filters were ashed for at least 10 hours in an LTA, while PVC samples were ashed for the 1.5 hour period known to be sufficient for membranes.

It was demonstrated that PDM and cyclone sampling systems produce substantially the same P-7 analytical assessments for quartz when run side-by-side. A correction factor was not required, because both sets of samples had the same degree of crystallinity and were assessed by the same technique, making a crystallinity-based correction factor inapplicable. The only spectral reference used was a PVCA filter; the ashed PDM filter had not show any benefit in the spectral subtraction process. Gravimetric assessments of collected mass between the two filter sets were also compared.

Tables III and IV summarize the spectrometric results of the PDM-collection tests. These tables compare P-7 analysis results for PDM nylon filters and the PVC reference samples. Table III reports the P-7 quartz results for both PVC and cellulose-backed PDM filters, and the percent difference between them. Table IV does the same for polyester-backed filters. (In these and other tables in the present disclosure, the subscript M denotes the mean of the measurements indicated). In general, quartz analyses for the two PDM filter types agree with the reference sample analysis within 2 percent. These two tables show that the 95 percent confidence interval for mean difference between reference and PDM P-7 results is within 4 percent.

Tables V and VI report collected quartz masses, based on gravimetric assessment of PVC filters and nylon PDM filters with the cellulose backing (Table V) and the polyester backing (Table VI). The tables also present the PDM instrumentally-assessed dust mass, based on the instrument end-of-file (EOF) data, which is the final instrumental mass reading for each test. These tables illustrate the PDM's instrumental accuracy with the new filters. The two tables show that the PDM- and PVC-filter gravimetric data agree within 3 percent. The 95 percent confidence interval for mean difference between PDM- and PVC-filter gravimetric results is within 4 percent. These figures were also recalculated excluding PDM unit 3, which showed aberrant EOF results, but the gravimetric comparison is little affected by this exclusion.

Tables V and VI also include a comparison of EOF readings to mean PVC gravimetric data. The EOF readings average about 10 percent higher, but within 7 percent, if an outlying unit 3 is excluded from the data. The two tables also include comparisons of EOF data to PDM-filter gravimetric assessments, on a unit-by-unit basis. The EOF readings are again somewhat higher, averaging within 12 percent, but within 8 percent, if the erratic unit 3 is excluded. Appropriate confidence interval data is also recorded in each table.

The particle size distribution of airborne Minusil-5 was also determined using model SE298 Marple cascade impactors (Thermo Electron Corp., Franklin, Mass.). Most of the Minusil-5 particles were in the respirable range below 5 µm in diameter.

These results demonstrate that the P-7 method is adaptable to use with the modified PDM filters and that the new filters are amenable to the intended analysis. Although longer ashing times are required for analysis of PDM filters than the PVC filters, the increased time requirement is manageable and may be further accommodated by using more efficient RF ashers, or laboratory planning for overnight ashing procedures.

When PDM and HD-cyclone quartz samples are collected in parallel, P-7 analysis yields very similar results for the two categories of samples, as shown in Tables III and IV. Hence the two types of samplers are collecting quartz particulates in the same manner. Tables V and VI record that the gravimetric evaluations of PVC and PDM samples are within 3 percent of each other. Hence sampling quartz particulates with PDMs is not subject to an unexpected sample loss, despite the long internal PDM sampling train. The results from parallel PDM and PVC sampling further demonstrate the suitability of ashable PDM filters for quartz analysis and the adaptability of the P-7 method for the new filter variations.

Although PDMs sample quartz particulates in an appropriate manner, there was a bias in PDM readings. Each PDM has an individual proportionality constant (called $K_0$) used by its software to convert changes in TEOM® frequency into collected dust mass measurements. If an alternative filter material has a different thickness from the EMFAB filter, the resulting radius of TEOM® vibration can be slightly different. $K_0$ can be changed to maintain accurate mass calculation. However it was found that $K_0$ values for the polyester backed filters were within 1 percent of those for EMFAB filters. Therefore calibration issues do not explain observed instrument deviation from gravimetric measurements.

It is believed that humidity effects are responsible for the deviation. The instruments' internal heating zones did not fully control the tendency of the nylon filters to pick up and release moisture. Because the PDMs do have an internal relative humidity sensor, the instrument software is modified to apply a humidity correction based on empirically-established filter response and the RH sensor reading, a process that can occur in real time. Even without this software correction, PDM measurement of collected particulate mass with the prototype filters does meet NIOSH accuracy criteria of being within 25 percent of reference measurements 95 percent of the time. However, the application of a real time software RH-based correction achieves substantially better accuracy. In some embodiments, the ashable filter material is modified for reduced sensitivity to ambient humidity, for example by using polyethylene or PP fiber having hydrophobic properties similar to the PTFE binder used in EMFAB filters.

The polyester backed filters were less sensitive to humidity effects than the filters that incorporated cellulose. Therefore noncellulose backed filters, such as those with polyester backings, are preferred in some embodiments.

Example 5

Examination of PDM Mass Reading Stability

In this example, tests were conducted to determine the inherent stability of PDM TEOMs when utilizing different types of PDM filters. These tests examined TEOM stability apart from environmental influence or electronic drift of the PDM instrument. Four PDMs were used, all in the same environment, side-by-side on the same table. The four PDMs all drew clean air from a common tube manifold, whose inlet was protected from dust with a large filter cartridge. Therefore, no actual dust was collected during the tests. Four consecutive runs were conducted on the same day, with all four PDMs operating synchronously during each run. Each test was 30 minutes long, during which mass readings were recorded by each PDM at 15-second intervals.

Standard fiberglass filters, polyester-back nylon filters, and cellulose-back nylon filters were utilized for the experiment. The three filter compositions were distributed among the four PDMs, so that one composition was placed in two PDMs and one filter of the other two compositions were each mounted in one PDM. The filter compositions mounted in the PDMs were changed with each progressive test. All filter specimens were tested only once as clean pristine samples. For the 16 tests conducted (four simultaneous runs with four PDMs per run), standard and cellulose-back nylon filters were each tested five times and polyester-back nylon filters were tested six times.

After data download from the PDMs, graphs of mass reading versus time were examined for linear trends. A convenient linear portion of each data file was taken for further processing. The best-fit linear equation for each data set was calculated and then this linear trend was subtracted from the source data that had produced it. This procedure served to remove any environmental or electronic influence on the data that occurred during the course of data collection. The residual data sets were consequently centered on average mass reading values of zero. The standard deviation of each modified data set was then calculated. The data scatter of each modified set, as quantified by the standard deviation calculations, reflected the stability of the TEOM-filter coupled unit, rather than other experimental influences.

Figure 12:
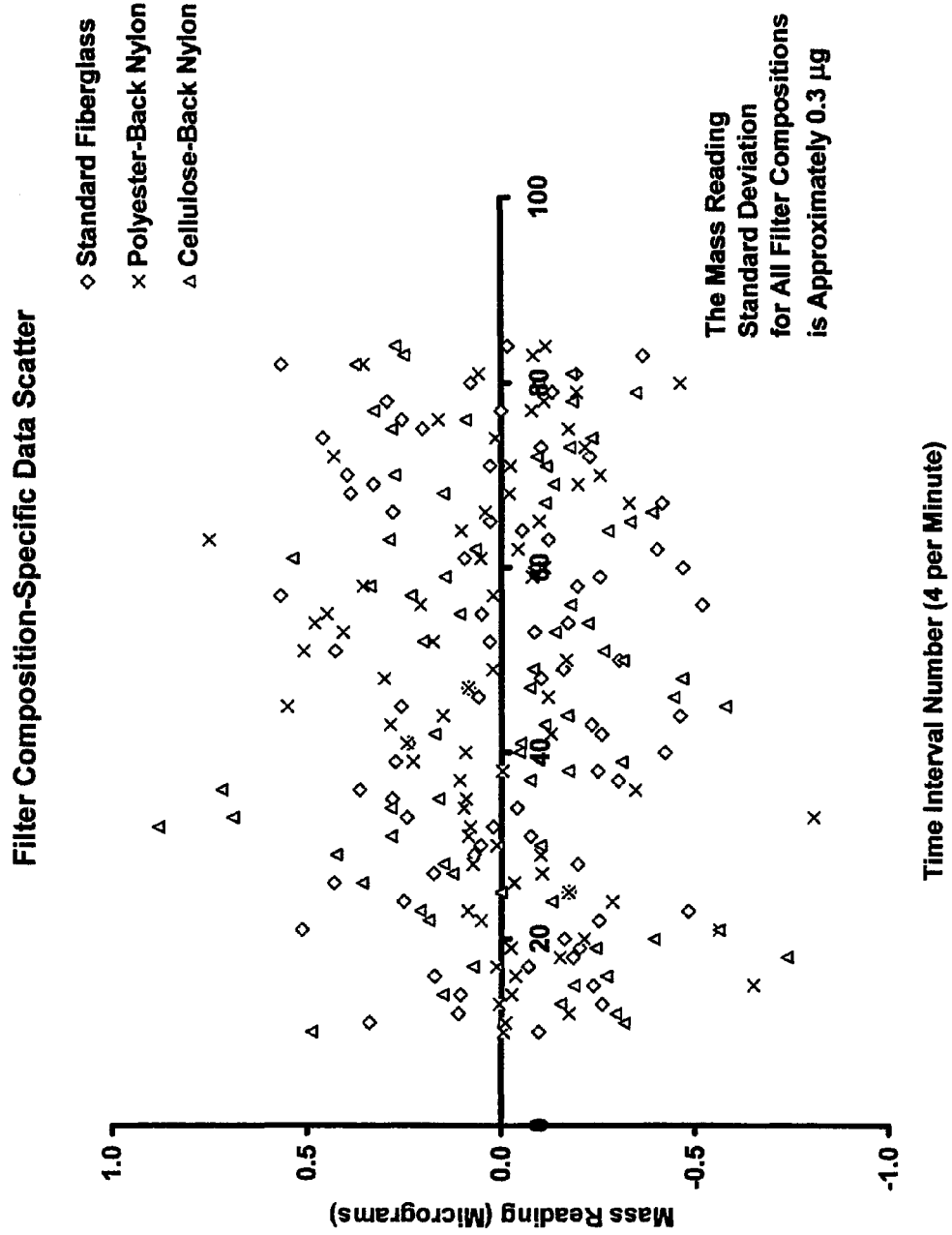
FIG. 12 is a comparison of the mass reading data scatter obtained with three different PDM filter compositions.

Tables VII and VIII summarize the standard deviation determinations, organizing them by filter composition, PDM unit, and test run. Generally speaking, mean mass reading stability (mean data standard deviation) can vary by 0.06-0.08 µg from test run to run or PDM unit to unit. Mean mass reading stability varied by only 0.03 µg in comparing filter compositions. The prototype filters tested caused no clear additional TEOM instability over standard filters, and no more than that already found in comparing different PDM units or separate runs of PDMs. Because the ranges for standard deviation values overlapped substantially for the data subsets examined, there might be no real differences in TEOM stability at all caused by filter composition. If there ultimately are actual minor differences, they appear to be changes in accuracy of only a few hundredths of a microgram. This is insignificant for all practical implementations of the PDM. FIG. 12 visually portrays three typical data sets for the filter compositions tested. The degree of mass measurement data scatter, and therefore the degree of TEOM stability, is essentially the same for the three data sets. All filter compositions produced data with standard deviations of about 0.3 µg. This suggests that no significant accuracy difference, or mass measurement sensitivity difference, exists between the filters, as relates to stability of TEOM-filter coupled assemblies.

Example 6

Humidity Correction

The PDM determines the mass of dust collected on its filter based on the change in frequency that occurs for the tapered element of its microbalance. As the mass on the filter increases with ongoing dust collection airflow through it, the frequency declines. The PDM does not immediately record mass readings when turned on. Instead, it first undergoes a 30-minute warm-up period. The PDM is programmed by the user to begin operating at a specific future point in time (typically during the same or immediately following day) and to operate for a specified time period. During the warm-up period, temperatures stabilize within the instrument as air flows through the filter. Because dust is collected on the PDM filter before the formal test begins, instrument calculations are referenced to the specified beginning of the actual test sampling time ($T_0$). $F_0$ is the TEOM frequency at $T_0$ and $M_0$ is the calculated collected dust mass at $T_0$, which is set to zero. The frequency $F_t$ of the TEOM at a point in time t is referenced to $F_0$ at the beginning of the test. The change in frequency from $F_0$ is used to calculate $M_t$ the collected dust mass at time t.

$M_t$ is calculated using the equation:

$$M_t = K_0 \times [1/(F_t)^2 - 1/(F_0)^2]$$

where:
$M_t$=the calculated collected dust mass on the filter at time t
$K_0$=a proportionality constant for the specific TEOM used
$F_t$=the TEOM frequency at time t
$F_0$=the TEOM frequency at $T_0$, the formal start of the test (after the warm-up period)
Using another appropriate proportionality constant, the collected dust mass may be expressed in desired mass units, such as milligrams or micrograms.

Figure 9:
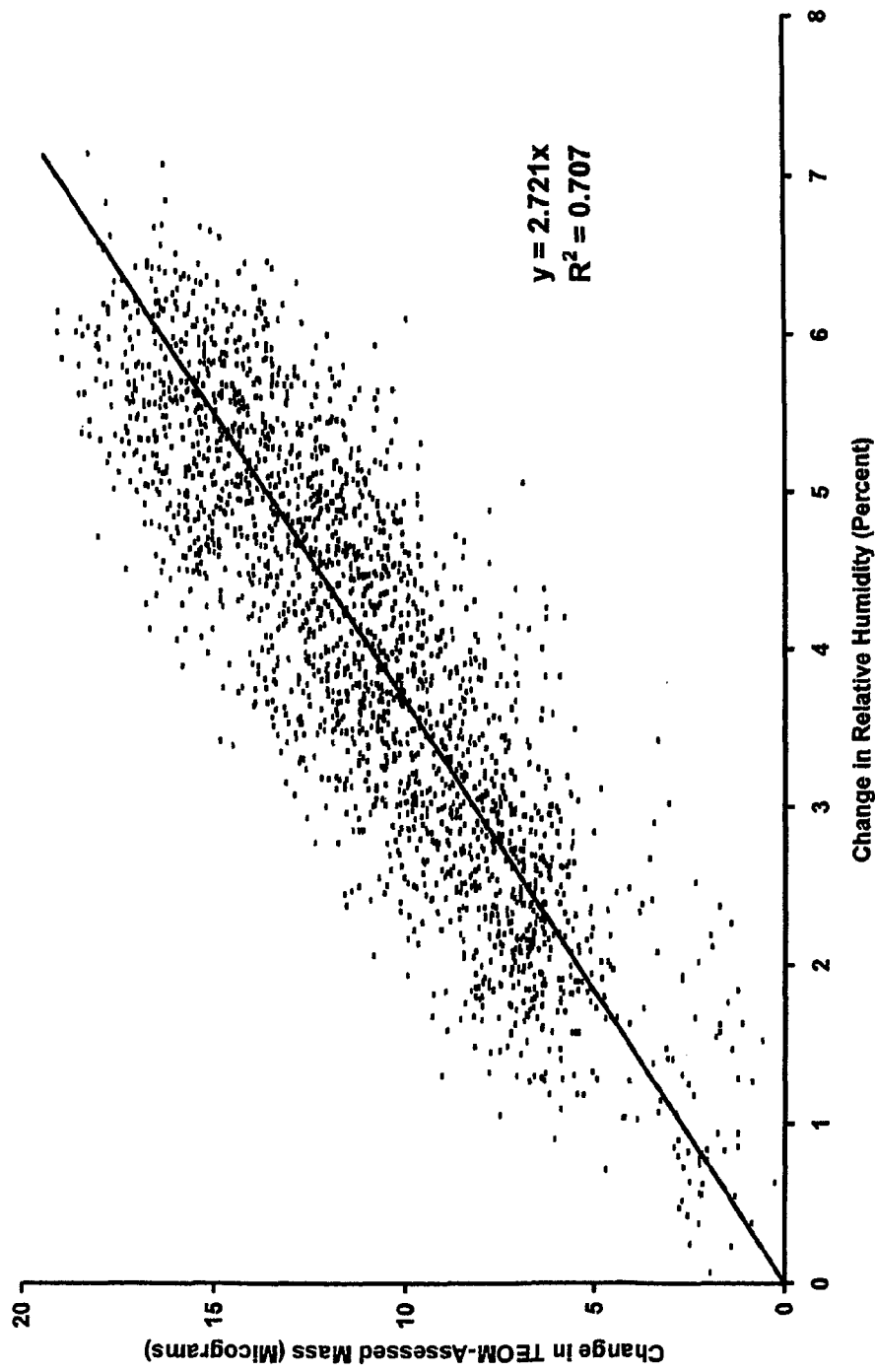
FIGS. 9 and 10 are graphs that illustrate a relationship between relative humidity and increased mass changes in microbalance filters that are made of different materials.
Figure 10:
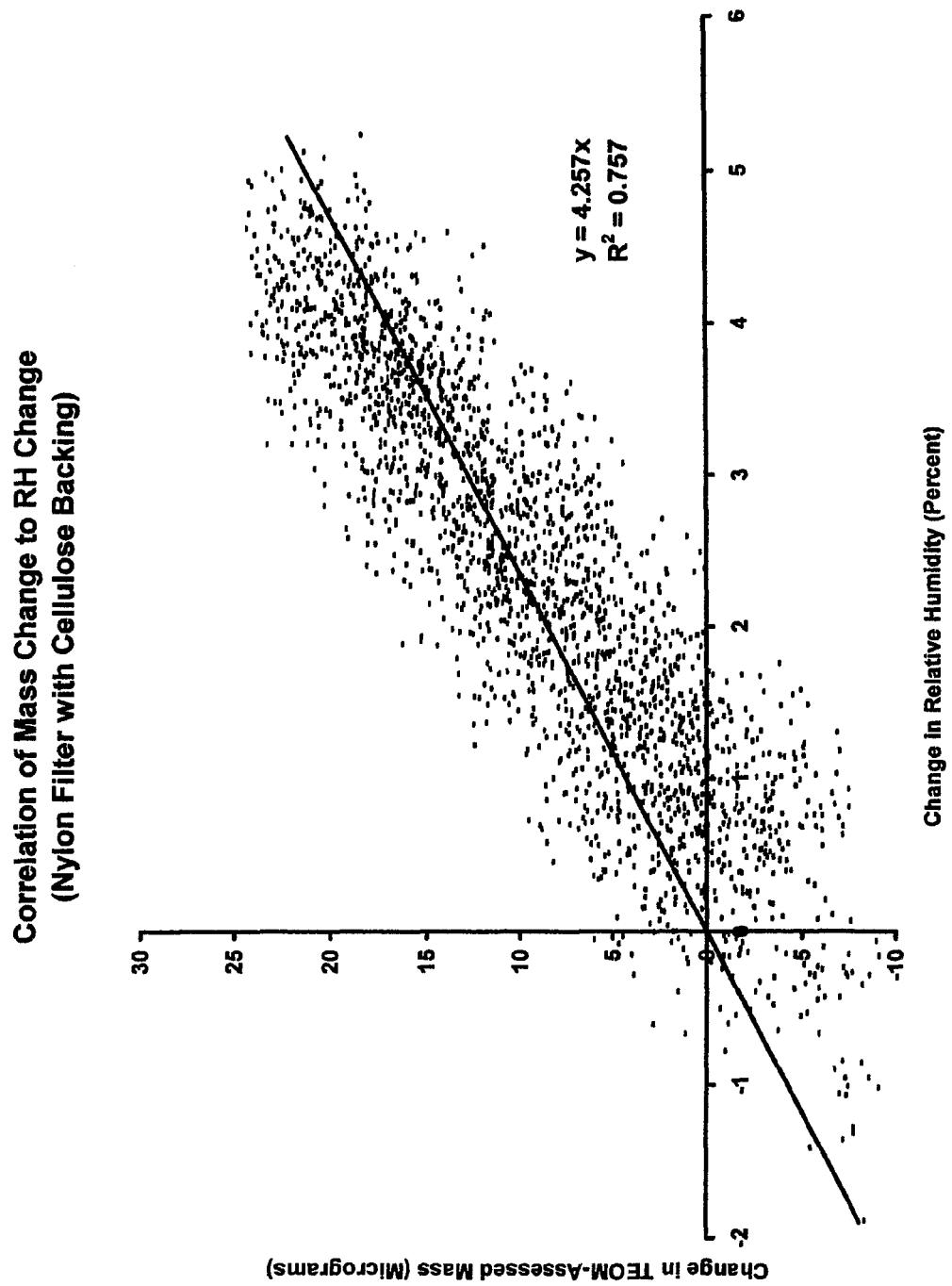

The mass calculation equation is modified, in accordance with a disclosed embodiment, to correct for environmental factors such as humidity. Because underground mines are typically moist environments where water sprays are used to reduce airborne dust concentrations, moisture-bearing air and particulates are commonly collected. The measured weight of the filter changes in a substantially predictable fashion in response to increasing relative humidity (RH) as shown in FIGS. 9 and 10. The change in mass is a function of both the RH and the composition of the filter. That relationship can be determined, as shown by the graphs in FIGS. 9 and 10.

In the present example, the PDM programming is modified to introduce a correction factor calculated from readings received from an internal RH sensor. This correction enhances the accuracy of mass determinations from the PDM, and permits greater flexibility in choice of filter materials. In particular, this correction allows less hydrophobic materials to be used as filter material, which in turn permits more optimal selection of filter materials that are suitable for destruction (such as thermal destruction) and spectrometric analysis without significant spectrometric interference. Other advantages of this technique are that the need to significantly increase RH-controlling airflow temperature is avoided, thereby reducing instrument power requirements, also thereby reducing loss of volatile particulate matter from the collection filter to warmer air, which would impair dust measurement accuracy.

The instrumental calculation of collected dust mass on the filter is performed using the equation:

$$M_t = K_0 \times [1/(F_t)^2 - 1/(F_0)^2] - H_t$$

where:
$H_t$=the humidity-related correction at time t for the now humidity-corrected calculated dust mass $M_t$.
$H_t$ is calculated by the instrument in real time, based on an empirical relationship:

$$H_t = E(R_t - R_0)$$

where:
$R_t$=the relative humidity at time t
$R_0$=the relative humidity at the formal start of the test, $T_0$
$(R_t - R_0)$=the change in relative humidity from $T_0$ time t
E is the empirical mathematical function applied to the quantity $(R_t - R_0)$ to determine $H_t$.

The relative humidity is determined by a PDM sensor, such as that at sensor block 50 (FIG. 3), but which may be placed in a number of locations inside or on the instrument. Because the humidity correction is applied to a filter in the TEOM portion of the PDM, the sensor is preferably close to the TEOM and in the same airflow. Although the sensor may be placed in a variety of locations, particular disclosed embodiments place the sensor in the path of airflow through the PDM, near or at the location of the microbalance (as illustrated in FIG. 3).

The PDM instrument measures and stores $F_0$, the frequency at the start of the test, comparing subsequent real time measurements $F_t$, to make use of the difference. The instrument also measures and stores $R_0$, comparing subsequent $R_t$ measurements to calculate the change in relative humidity. Both frequency and relative humidity measurements are referenced to the start of the test at $T_0$. Regardless of actual moisture mass on the filter fibers at $T_0$, the instrument records $F_0$ and sets the initial filter-plus-moisture mass to zero. Subsequent time points in the test provide collected dust mass measurements calculated from changes in both TEOM frequency and relative humidity, both making use of the differences from those at the test start. If relative humidity is greater at time t than $T_0$, then $E(R_t - R_0)$ is positive, and that quantity would be subtracted from the calculations for dust mass. If humidity is lower at time t than $T_0$, then $E(R_t - R_0)$ would be negative, and subtracting that quantity would result in a positive correction in the calculations for dust mass.

An empirical process is used to determine the function E by which the humidity-related correction is calculated. Because filter material is generally manufactured in sheets or rolls, product specifications for material density and filtration efficiency are typically average properties for large specimens or sheets. However, for the PDM filter application, a very small filter size is typically used (an open-face diameter of only 14.0 mm). To avoid filter-to-filter differences, it is desirable for the parent material to be as uniform as possible. PDM filters are already subjected to quality control procedures to ensure collection efficiency and low airflow resistance, but humidity response has not previously been determined. To perform this procedure, a numerical sample size determined by common statistical methods is selected to find the average response of filter units to humidity change. The more uniform the manufactured filter material is, the smaller the sample size can be.

Each filter test sample is mounted into a PDM and a sampling run initiated, with an extra intake filter placed upstream of the test filter to prevent accumulation of dust from the air on the test filter. The humidity reaching the TEOM is then intentionally altered to determine the humidity effects on instrument-calculated dust mass, and the PDM-calculated deviation from zero dust mass is recorded. For example, the test PDM is placed in an environment (such as a test chamber) where the relative humidity oscillates periodically. Alternately, a water bubbler or other source of humid air may be attached to the PDM inlet, inducing minimal airflow resistance and differential pressure, while drawing moisture into the airflow path within the PDM. The water bubbler is detached and reattached periodically to produce a step function for the instrument's internal humidity.

The use of a bubbler allows the humidity to be changed between two wide settings. The oscillating environment also allows active change over many less dramatic transient humidity levels. Either test is adequate for determining a humidity correction factor for the filter, although both tests may be performed as mutually confirming assays (empirical determinations). The changes in measured mass versus internal RH for each time point in the test are plotted. This approach involves no significant time lag between measured RH and filter response to RH.

Alternatively, assays can be performed to take into account certain filter mass changes that occur in response to RH in a less than immediate manner. In such an assay, collected data is examined to reveal an optimum relationship between RH and filter mass. $R_t$ is correlated to $M_{(t+d)}$, where d is the time lag or delay period applied to time t. For particular filter materials, in which there is a more complex relationship between RH over time and the filter mass, a time integration of RH over the time span in question may be performed. Alternatively, a time-weighted average of RH is used. Filter materials usually have a direct correlation between RH and filter mass change, with minimal time lag, which is readily represented by a straight-forward equation. The equation may be linear, polynomial, exponential, or possibly some other mathematical function. When the plotted equation passes through the origin, zero change in RH causes zero change in measured mass of the filter.

In a particular example, the relationship between filter mass change and internal relative humidity was determined through an environmental oscillation approach. The results are shown in FIGS. 9 and 10 in which linear correlations pass through the origin. For polyester-backed nylon filters, a mass change of 2.721 micrograms occurred for each 1.0 percent change in RH, that is, $H_t = 2.721 \times (R_t - R_0)$ when mass is expressed in micrograms. For cellulose-backed nylon filters, a mass change of 4.257 micrograms occurred for each 1.0 percent change in RH, that is, $H_t = 4.257 \times (R_t - R_0)$ when mass is expressed in micrograms. Respectively, the Coefficients of Determination are 0.707 and 0.757 for the two types of filter. The correlations predict the mass changes within a few micrograms, fully suitable for occupational health monitoring purposes and many other applications of TEOM-based instruments. (Note that a common notation for Coefficient of Determination is $R^2$, which should not be confused with our notations for relative humidity $R_t$ and $R_0$.)

In other embodiments, stronger mass-humidity correlations are achieved by incorporating more accurate sensors into the PDM or modifying their data recording method. For example, a more stable RH sensor is employed, or the time averaging period for the RH sensor is lengthened to further reduce data scatter. In other examples, the time averaging period for the TEOM frequency calculations is lengthened, or the RH sensor and TEOM are synchronized with each other to have the same time averaging and data-recording periods.

For the PDM as it currently records data, the algorithm for calculating collected dust mass is:

$$M_t = K_0 \times [1/(F_t)^2/(F_0)^2] - [C \times (R_t - R_0)]$$

for filters with a linear mass-RH response relationship. C is a filter composition-specific proportionality constant.

Example 7

Filter-Specification Software for Rapid Modification of PDM

PDM 20 is a programmable electromechanical instrument that is provided with its own software. Many instrument functions can be initiated by pressing buttons and viewing a small screen on PDM faceplate 26, but accessing full instrument flexibility is usually achieved using a communication link with a personal computer (for example through an attachable cable that affixes to electrical contacts between the metallic belt clips). The instrument software, called "WinPDM," operates in a Microsoft Windows® environment. It enables the user to program a PDM for sampling runs, collect data in a specific manner, and apply quality control procedures to instrument performance. The user can navigate between several visual screens, each being a Graphical User Interface (GUI), to modify and enact the desired mode of instrument operation. The most relevant interfaces for controlling the instrument, and describing the invention, are discussed below.

An initial surface-level GUI is the Operation Selection Screen. It informs the user about the connection status (communication link) between the PC and the PDM, as well as the instrument operational status (for instance, whether it's scheduled or unscheduled to begin a sampling run). This interface also accesses other key GUIs that program a start time, change operation features, download sampling run records, and calibrate the instrument airflow.

A deeper level GUI, the Program Shift Screen, enables the user to set a date and time for the next sampling run to automatically begin. It has multiple data entry fields to fully identify the sampling run that will occur. It also has a GUI element for the user to select a temperature range that will characterize the environment where the test will occur, in that this environmental factor may vary from test to test.

Another deeper level GUI is the Configuration Screen. The PDM is capable of recording data for a wide variety of variables. Microbalance resonance frequency, collected dust mass, calculated airborne dust concentration, airflow rate, temperature, relative humidity, filter differential pressure, and atmospheric pressure are among the many instrumental and environmental parameters for which data can be gathered. The selected parameters are recorded or "logged" into a PDM data file with user-selected time frequencies that can vary from every few seconds to every few minutes, or even longer periods. The logging procedure can be set to varying sensitivity, in regard to changes in parameter readings. The instrument can record every minor change in measured parameter readings, or record only major changes, if desired. This GUI enables the user to extensively modify logging parameters, or choose a template for logging parameters. A "template" is a small user-selected or user-generated file containing a full set of logging parameters, which determines what kind of data the PDM will record and in what manner the recording will occur.

To enhance PDM flexibility in accommodating different types of filters, this example provides a readily manipulated approach for adjusting the PDM when a filter is used that is suitable for post-sampling spectrometric analysis of collected dust particles. Instead of the user changing relevant parameters by deliberately making each individual change in existing software interfaces, a single specialized GUI element is provided to select the type of PDM filter being used. Selection of the filter type automatically institutes a series of parameter changes that avoid more time-consuming manipulations through existing interfaces.

In a particular example, the filter-selection GUI element is a check box, drop-down menu, or other visual user-selectable data input device. It is capable of incorporating multiple possible filter-selection options. Therefore, the user can make one selection when the type of filter being used is for post-sampling quartz analysis, and another GUI selection when a standard Teflon/fiberglass filter is employed. In other examples, additional GUI-element selections are incorporated for other special-purpose filters. For instance, the GUI may present a series of checkboxes, one for each possible type of filter, or a drop-down menu revealing a list from which to make a filter selection. The filter-dedicated GUI element may be placed in any of the three interfaces discussed above, or provided in a separate dedicated interface. Providing the filter-selection feature in a user-accessible screen avoids the necessity of making multiple separate parameter changes. Once a filter selection is made by the user, the selection is preferably visible to the user reviewing the interface screens, rather than being a hidden software feature. The filter selection is recorded in the data file ultimately generated by the PDM, which provides additional information for evaluation of the data collected in the file.

In the disclosed example, the filter-selection GUI element implements changes to instrument calculations and operations that optimize PDM instrument function for use with the selected type of filter. This may involve both firmware and data manipulation (or recording) functions. For example, a change in filter composition alters the $K_0$ the instrument uses, where $K_0$ is the proportionality constant that relates TEOM instrument frequency changes to calculated dust mass on the PDM filter. A specific humidity-based correction factor can be used for each different type of filter to improve accuracy in calculating collected dust mass. In some embodiments, the temperature applied to the TEOM instrument is changed, or the time averaging periods for evaluating TEOM frequency and outputs of other PDM sensors are varied. In the disclosed embodiment, all the filter-specific changes are associated with and implemented by changing the selection in a dedicated GUI element. This interface feature adds versatility while reducing complexity, which is particularly advantageous for less trained users. The ability to quickly implement different instrument operational functions allows the instrument to be readily adaptable for using filters that are specifically suited for quartz analysis or other special applications that require filter composition switches, while avoiding an instrument design that is operationally more complex or less accurate.

Example 8

Filter Recognition and Utilization Capability

Some embodiments of the PDM provide a means for readily distinguishing and utilizing different types of filters or even automatically recognizing and utilizing the type of filter that is placed in the TEOM instrument or other microbalance device. Recognition of different types of filters is often difficult because many different filter types are superficially similar in appearance. For example, fiberglass filters may have a white surface while nylon filters are beige, with no other readily visible distinction. Nylon fiber filters that have a polyester backing appear substantially identical to nylon filters with a cellulose backing. Because the filters differ only in their hidden enclosed backings, their external appearances are essentially identical.

This problem is addressed by manufacturing different types of PDM filters with deliberate detectable differences in appearance to render them more readily distinguishable. Different filter assembly components, or filters made of different materials or with different backings, may be fabricated to include fully-organic pigment or colored dye. A particular dye color is associated with a particular type of filter. For example, a nylon filter with a cellulose backing is mounted in polypropylene components, one or both of which is dyed red, or a nylon filter with a polyester backing is mounted in polypropylene components, one or both of which is dyed blue. Alternately, the filter disks themselves may be dyed, apart from appearance modification of mounting components.

Particular examples of organic pigments that may be used for this purpose include: carbon black, lamp black, acetylene black, finely ground graphite, and powdered charcoal. A variety of carbonaceous materials of sufficient purity or low cost might be used. Materials of this general type are part of rubber tire manufacture, often included as reinforcing fillers, but also leaving obvious color evidence of their presence. In the case of marking PDM filter components and identifying different types of filter assemblies, it could be sufficient if traces of the pigment achieved merely a gray tint to the final component appearance. Carbonaceous materials are also known to have a degree of electrical conductivity, giving them antistatic properties. This could make filter assemblies easier to gravimetrically assess, in that static charge often interferes with weighing.

Innumerable organic dyes are commercially available for the coloration of fabrics, foods, and plastics (including nylon). Specific color is quite unimportant and only a cosmetic consideration. The dye is selected to adequately mix with hydrophobic melted nylon, survive the heat of mixture and injection molding, and be as fully organic as possible, ideally without metals in its composition. This last criterion helps minimize the residual material after ashing, and prevents interferences when metals analysis of collected dust is a consideration. Only a trace of dye additive is needed in one or more PDM filter components, to achieve a change in appearance and facilitate identification.

Alternatively, a particular type of filter may be recognized by the PDM based on a characteristic mass of a particular type of filter (such as a Teflon/fiberglass filter compared to a nylon filter with a polyester backing). In some embodiments, the PDM is programmed to automatically adopt a corresponding set of parameter changes appropriate for the type of filter identified. For example, a particular $K_0$ is associated with a filter having a particular mass. When using this approach, different filter types are used that have distinctive mass ranges that do not overlap.

For example, in an extremely dusty environment, a PDM filter may collect 6 mg of dust over the course of a sampling run. Therefore, if two types of filter assemblies inherently differed in mass by 10 mg or more, the PDM is readily able to identify the filter assemblies based on their mass, as derived from microbalance vibration frequency. The mass difference between filter types would partly originate from differences in the filter pads they incorporated. However, heavier or lighter polypropylene components could also be incorporated into the assemblies to enhance (or reduce) mass differentiation.

In one example, type-A filters have a clean mass range of 104-112 mg and a nonclean mass range of 104-118 mg (which reflects the amount of dust collected on the filter in a particular environment). Type-B filters have a clean mass range of 125-133 mg and a nonclean mass range of 125-139 mg (which reflects the amount of dust collected on the filter in a particular environment). The mass ranges for the two types are designed not to overlap whether the filters are assessed in a clean or dust-deposited condition. The heaviest mass of type-A filters never reaches the lightest mass of type-B filters (118 mg versus 125 mg, in this case). A microbalance-based instrument (such as a TEOM instrument) is able to distinguish between the two filter types based on mass alone. Similar mass range differences are used to distinguish other filters when more than two filter types are potentially used in the device. The precise mass ranges appropriate for filter types may of course be narrower or broader than the specific examples provided. Implementation of this automatic filter recognition feature can take into account the actual heaviest dust mass expected, the margin of safety desired between filter-type mass ranges, and the acceptable filter mass and frequency ranges for the TEOM microbalance itself.

After a filter is mounted in a PDM, the instrument is then programmed for a sampling run. The instrument is activated and starts a 30-minute warm-up period before the programmed sampling time begins. At $T_0$, the beginning of the formal sampling run, the instrument determines $F_0$ (the microbalance frequency at $T_0$), which serves as the reference frequency for the duration of the test. Before or simultaneous with the instrument determining $F_0$, a software operation also identifies the filter type. Each filter type has a characteristic microbalance frequency range, reflecting its characteristic mass range. Before or at $T_0$, the filter identification initiates instrumental operational parameters appropriate for the filter type the instrument recognized. The data file generated by the instrument records the filter identification as one of the core informational elements for the sampling run. As an option, the instrument may display the filter type on an external view screen, or in various software screens, so the filter identification is also confirmable by means other than the final data file.

Different types of filters may have different sensitivities to humidity, which would affect their mass. However, the assessment of filter mass can be optimized if interim mass calculations employ parameters best suited for the task of filter identification. Filter identification can occur during the warm-up period, or at $T_0$, under a standardized set (or one of several standardized sets) of instrumental conditions and with some standardized set(s) of calculation parameters. The interim parameters need not be a final set of parameters for any type of filter. In some embodiments, filter identification occurs late in the warm-up phase to help assure that steady state conditions have been reached. The measurement of the initial filter mass (or microbalance frequency) is compared to an index or table of value-ranges (in instrument memory) for various types of filters to identify the filter type that is present in the instrument. The mass calculations do not have to be fully accurate during the filter-identification phase of instrument operation because it is adequate if they are only accurate enough to correctly identify the filter type.

In a particular embodiment identification of filter type initiates automatic software-controlled adoption of correct instrument parameters without additional user input. An example of an instrument-selected operational parameter is the filter-specific $K_0$. Other operational parameters can include one or more of: instituting a humidity correction, changing a temperature setting applied to the microbalance, adjusting the time period for averaging microbalance vibration measurements, or other desired variations in instrument operation or data processing. In specific embodiments, the number of changes adopted reflects the degree of difference in the types of filters employed. When significant changes to the instrument's internal environment are involved, such as changes in internal temperature, it is preferable that filter identification be performed earlier in the warm-up period. This allows more time for the instrument to equilibrate to its adopted operational mode for the pending test run. The invention may be implemented during early, middle or late warm-up, for whatever balance of interim and final stability are desired.

Alternate embodiments of the invention may make use of other filter characteristics to achieve filter recognition. Filter type identification by the instrument may be based on filter airflow differential pressure, physical dimensions, or other characteristics or combinations of filter assembly characteristics.

Another embodiment of the PDM makes more versatile use of its removable TEOM microbalance 46 than now implemented. Currently, ready access to the TEOM unit simply allows rapid switch of filters between sampling runs, and facilitates cleaning the internal air spaces of the instrument. Each TEOM microbalance is mated with a larger instrument apparatus (in the main housing 22) with its operation requiring use of a programmed mathematical constant $K_0$ appropriate for the specific TEOM unit involved. This limited use of removable TEOMs is based on maintaining minimal differences in the properties of filters (and their filter assemblies). In another embodiment, TEOM design is modified to accommodate successful use of different filter types that would otherwise provide inaccurate data without changes in instrument design and operation.

A removable TEOM is modified to accommodate filter assemblies of different composition(s) and/or properties. Such filter assemblies may have, for example, heavier or larger filters constructed of other than fiberglass material for analysis of one or more analytes. In this embodiment, the TEOM tubular element may be modified to produce a different resonant frequency, or may function best with different operational parameters. The removable TEOM has physical features that aid in identification and successful use of different filters. The removable TEOM's own external housing surface is modified to display color markings that match the colors of the filter types that may successfully be used with it. It may also have a specific identifier or encoding device that when mated with the larger instrument, causes the TEOM type (and therefore the filter type) in use to be identified by the instrument.

The identifier may be a physical feature. This may be, for example, a stem of specific length, recess of specific depth, or specific arrangement of multiple pins or recesses. Alternately, the encoding device may be an electrical resistor or other electrical component with specific properties, or an electronic chip or memory storage device. The main instrument body mates with the TEOM unit, assessing or interrogating its specific physical or electronic features. It thereby identifies the TEOM unit and correctly assumes the type of filter in use. It then begins automatically functioning with a new and correctly modified set of operational parameters appropriate for the TEOM unit and filter type it identified. If a memory storage device is utilized, the device may transmit necessary operational settings to the instrument for the specific TEOM involved. The sampling data file generated by the instrument records the TEOM type and/or filter identification as core informational elements for the sampling run. As an option, the instrument may display the TEOM and filter types on an external view screen, or in various software screens, so the information is also confirmable by means other than the final data file.

The PDM may be provided in a kit which contains multiple removable TEOMs for a variety of filter types and purposes.

Example 9

Analysis-Facilitating Sample Transport Containers

While the measurement of total dust exposure occurs immediately at the sampling site, the analytical determination of quartz (or other analyte) content of the dust is usually performed at a different location where a spectrometer (or other analytical instrument) is located. For example, analysis for the quartz contribution to the collected dust mass occurs at a remote laboratory. To maintain the accuracy of the analytical determination, methods and devices are disclosed herein for transporting and which facilitate processing the filters without significant loss of particulate sample.

In one embodiment shown in FIG. 7, the filter assembly 108 is placed in a low-mass enclosure 140 such as a small bag or envelope structure having a self-sealing flap 142. Adhesive material 144, 146 is present on one or both of enclosure 140 and flap 142 to enhance adherence of flap 142 to enclosure 140. The adhesive material may be selectively covered by protective strip(s) to avoid premature sealing of enclosure 140 until filter assembly 108 is placed in it and the protective strip(s) removed. At the sampling site, the filter assembly 108 is removed as a unit from the PDM in which it was used, placed into the shipping enclosure 140, and sealed by adhering the self-adhering flap 142 to the body of enclosure 140. The enclosure is then transported to an analytical laboratory where both the enclosure and the PDM filter assembly it holds are subjected to thermal destruction and the resulting residual ash is subjected to spectrometric analysis.

A clean organic PDM filter assembly has a mass generally under 115 mg, and even with collected coal dust the mass is generally no more than 120 mg. In preferred embodiments, enclosure 140 has a mass of no more than approximately one gram to help minimize additional ashing time that may be required to ash enclosure 140 along with the filter. The enclosure is preferably made of a fully ashable material. A variety of polymers are viable low-ash candidate materials, as demonstrated by ashing tests discussed above. Alternatively, specialty papers, fabrics, or even nitrocellulose membranes could be used. The material that is selected is fully ashable by readily available means and introduces no spectrometric interferents into the residual ash. The enclosure material (for example a dust impermeable polymer) forms a dust-tight receptacle for the filter assembly.

In addition to the self-adhesive enclosure illustrated in FIG. 7, other embodiments of the enclosure include a plastic bag 150 shown in FIG. 8 in which a polymeric material is gathered at 152 and closed with a wire-like twistable tie 154 that is subsequently removed after arrival of the enclosure at its destination and prior to the ashing procedure.

Another embodiment is shown in FIG. 5 in which a relatively low volume plastic cup 160 serves as the enclosure. Cup 160 mates with adequate tolerance with a plastic lid 162 as shown in FIG. 6 to provide a substantially sealed enclosure. In this example, a plastic projection 164 protrudes upwardly from the rinsable bottom inner face 166 of cup 160 to provide a mounting on which axial hub 114 of filter assembly 108 is placed to secure filter assembly 108 in cup 160 during transport. Lid 162 is secured over cup 160 with sufficient tightness that the resulting enclosure substantially completely retains any dislodged dust along with the PDM filter assembly to avoid dust loss during shipping.

In this embodiment, the enclosure has smooth rinsable interior surfaces that are readily cleaned with a rinsing surfactant or solvent (such as isopropyl alcohol) to avoid leaving dust residue in cup 160 or on lid 162 that would impair the accuracy of quantitative analysis of analyte on filter assembly 108. Although the plastic cup illustrated in FIGS. 5 and 6 would be suitable for this purpose, many rinsable sealable shipping enclosures could be used, such as: a bottle, jar, canister, box, or more shallow structure. At the sampling site, the filter is removed from the PDM in which it was used, placed into the rinsable sealable shipping enclosure, and transported to a remote analytical laboratory. After arrival at the analytical laboratory and removal of the filter assembly, the interior of the enclosure is rinsed, washed, or swabbed to dislodge dust from the interior of the enclosure. The dust-bearing rinsing fluid is then added back to the filter assembly. Once the rinsing fluid has dried, the filter assembly and recovered dust are ashed together.

In this embodiment, the enclosure need not be made of a low mass material because the enclosure is not ashed. Freed of such limitations, the enclosure in this embodiment may be made as rigid and protective as desired as long as the enclosure material is resistant to damage from the rinsing or cleaning process and thereby facilitates a complete dust sample recovery. Isopropyl alcohol is currently a preferred surfactant for dust rinsing, because it is a low surface tension solvent that is suitable for removing very fine dust from surfaces to which it clings, overcoming electrostatic adhesion of the dust. Other solvents or solutions also have suitable surfactant properties. The enclosure may be made from glass, plastic, metal, or any material suitably resistant to rinsing with dust-removing surfactant.

The rinsable shipping enclosure can assume a variety of configurations. It may hold the PDM filter assembly loosely or it may have a means to fix the filter in a particular position (such as an interior tube, well, spindle, or perch, either solid or hollow, which suitably serves to secure the stem or other portion of the PDM filter assembly). For example, it has a tube at its inner base into which the PDM filter assembly stem is inserted. It may have a well to loosely hold the filter stem, along with a screw-on or pop-down lid that presses the PDM filter into a substantially fixed position within the enclosure. If the PDM filter assembly is held in a fastened position, it may be advantageous if the interior of the enclosure is sufficiently large to permit a removal tool (such as a fork) to be inserted into the enclosure under the mounted filter assembly for its removal from the enclosure. The inner construction of the enclosure avoids excessive dimensional volume and inaccessible recesses which might make any dislodged dust more difficult to recover.

The enclosure fully retains the dislodged dust along with the PDM filter assembly, thereby avoiding dust loss during shipping. The enclosure is also chemically compatible with the surfactant employed to remove the dust from the enclosure, such that the enclosure does not significantly degrade with rinsing-duration exposure to the solvent. It is also desirable that the enclosure not have consequential surface properties (such as strong electrostatic charge, or rough texture) that would substantially interfere with rinsing away surface dust. Many variations in structure and composition are possible in meeting these criteria.

Figure 13:
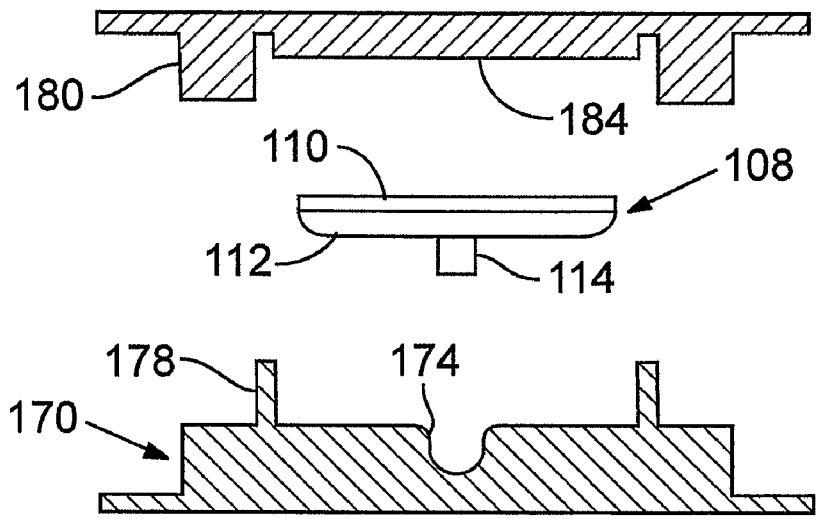
FIG. 13 is a side view partially in cross-section of a dust-securing container for transporting the filter and its mounting platform, according to another embodiment. The container's removable sample-contacting lid has been removed to place the filter and platform assembly in the container.
Figure 14:
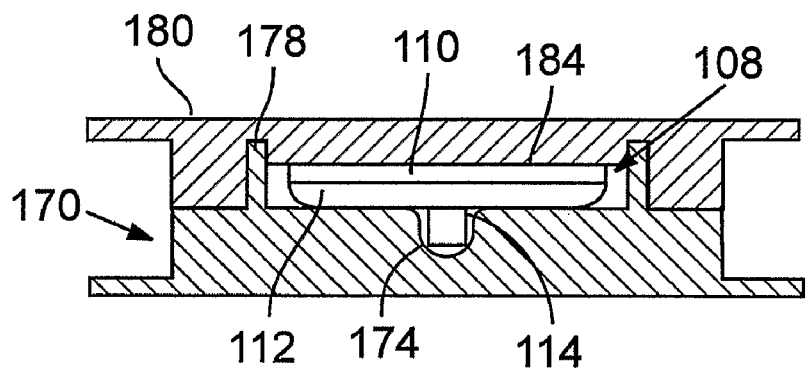
FIG. 14 is a view similar to FIG. 13, but showing the filter and mounting platform within the dust-securing container, and the sample-contacting lid held tightly in-place covering the opening in the container.

Yet another embodiment of a substantially rigid rinsable container or enclosure is shown in FIGS. 13 and 14. In FIG. 13 a relatively low volume plastic receptacle, or base, 170 serves as the base for an enclosure. A plastic lid 180 is adapted to cover the opening of the base 170. Base 170 desirably mates with adequate tolerance with lid 180 so as to provide a substantially sealed enclosure when fully closed, as shown in FIG. 14. In this example, a contoured surface 174 comprises the center of the rinsable inner face of base 170 to provide a region adapted to loosely receive a protruding axial hub 114 extending from assembly base 112 of filter assembly 108. Lid 180 in the illustrated embodiment forms a frictional fit with an upstanding annular wall 178 of base 170 and desirably is secured over base 170 with sufficient tightness that the resulting enclosure substantially completely retains any dislodged dust along with the PDM filter assembly to avoid dust loss during shipping.

In the illustrated embodiment, a rinsable lid inner surface 184 physically contacts filter assembly 108 upon full closure with base 170 and substantially retains dust from filter 110 in the proximity of filter 110 so that dust material is less likely to drift throughout the enclosure during shipping. Dislodged dust remains above filter 110 and is substantially sealed in a small localized region at the center of lid inner surface 184. This facilitates dust sample rinsing and makes quantitative dust transfer for analysis more readily achieved. A special filter assembly mounting tool is not needed to remove filter assembly 108 from receptacle base 170. This has the advantage of reducing dust sample loss, particularly dust transfer onto the mounting tool from accidental filter-scraping or jerking motions during sample handling when a mounting tool is employed.

Figure 15:
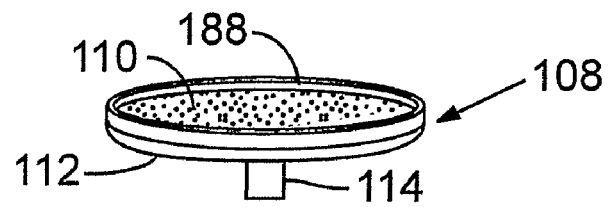
FIG. 15 is a perspective view of a filter and mounting platform assembly unit, according to one embodiment.

FIG. 15 shows a perspective view of a filter assembly unit 108, as viewed from above, which can be used in the disclosed embodiments. Filter assembly 108 includes a circular filter mat 110, which is shown having dust deposited on its upper surface. Filter 110 rests upon and is sonically welded to assembly base 112 and is also sealed against peripheral airflow leakage by a ring 188 around the circumference of both filter 110 and base 112. Filter 110 is substantially at the top of filter assembly 108 and acts as the air intake surface of filter assembly 108. Axial hub (or stem) 114 is at the bottom of filter assembly 108 and serves as a short tube through which air is drawn during sample collection when the filter assembly 108 is mounted and used in a PDM. Ring 188 in this embodiment provides a measure of protection to filter 110 because the upper surface of the filter 110 is slightly recessed below the upper surface of the ring 188. Therefore, the means to handle filter assembly 108 without a special tool that may disturb collected dust and the means to fully recover dust dislodged during sample transport are both advantages which accommodate the limited protection of a dust sample on filter 110.

The inner construction of the enclosure shown in FIGS. 13 and 14 provides enough room for easy sample transfer, but avoids excessive dimensional volume and inaccessible recesses which might make any dislodged dust more difficult to recover. The enclosure also has smooth rinsable interior surfaces, without strong electrostatic properties, which are readily cleaned with a compatible rinsing surfactant or solvent (such as isopropyl alcohol). This avoids leaving dust residue in base 170 or on lid 180 that would impair the accuracy of quantitative analysis of analyte on filter assembly 108. The enclosure may be made from plastic, metal, or any material suitably resistant to rinsing with dust-removing surfactant. In this embodiment, the enclosure need not be made of a low mass material because the enclosure is not ashed. Without mass limitations, the enclosure may be made as tight and protective as desired, sealing appropriately, and adequately securing the filter assembly and its dust, as long as the enclosure material is suitably resistant to the final rinsing process and thereby facilitates quantitative dust recovery.

For example, screw threading features or circular groove locking features may be incorporated as sealing mechanisms for a mated base and lid to achieve dust-sealing pressure onto an enclosed filter assembly and ensure dust-retention during transport. Also, a lid interior surface may be contoured to enhance a sealing fit with an enclosed filter assembly. Many variations in container structure and composition are possible in meeting functional criteria, fully amenable to the sampling site, shipping, rinsing, and sample analysis procedures described earlier for rigid rinsable sample containers.

Information obtained from the samples may have legal implications in liability law or occupational health law enforcement. In some embodiments, the shipping enclosures are made tamper resistant. For example, each enclosure is sealed with an indicator (such as an adhesive seal) that indicates whether the enclosure is opened between the time it is initially sealed and when it reaches a destination (such as an analytical laboratory where spectrometry is to be performed). Particular embodiments of the tamper indicator are an adhesive spot, flap, or encircling thread or band that is part of or affixed to the enclosure. In other embodiments, the shipping enclosures are placed in larger sealable receptacles. The PDM may be provided in a kit which contains rinsable or ashable shipping enclosures, as well as larger receptacles for holding the shipping enclosures.

Example 10

Other Analytes and Analytical Methods

The method of determining a mass of dust and identifying one or more components of the dust can be used for detecting a wide variety of analytes using a variety of analytical methods. Although examples of the use of the method and device have been provided in the context of occupational exposure to coal dust, these examples are not intended to limit their use to that type of application, or even generally to occupational heath sampling implementations. In addition, there are many general environment-assessment applications that do not require a PDM. Any target material that would survive a preselected ashing or chemical digestion process could be considered as a candidate analyte. Examples of such target materials would include most minerals, metals, and some inorganic compounds.

For instance, if dust is collected on a PDM filter and subsequently ashed, the residue may be analyzed by infrared spectroscopy or X-Ray Diffraction (XRD). In the case of IR, the residue may be redeposited on a suitable organic filter and examined in an IR spectrometer. Alternatively, the residue may be mixed with potassium bromide (KBr) salt and pressed into a pellet, then examined in an IR spectrometer. In the case of XRD, the residue would be redeposited onto a silver membrane filter, and the sample in that form examined in an XRD spectrometer. Raman spectroscopy can be used in many cases when IR is used, and is often a complementary method to IR.

To perform an analysis for quartz, current methods also determine kaolin clay. Kaolin is very common in coal mine dust samples. Its IR bands partly overlap with quartz. Therefore, the analyst corrects the quartz determination for whatever influence originated with kaolin, for example as part of the earlier described P-7 method. There are other forms of crystalline silica that also present health concerns. These crystalline silica polymorphs (sane $SiO_2$ elemental composition, but different crystalline structures) are called tridymite and cristobalite. They are not generally found in coal mines. Although quartz is the more abundant mineral, the other two polymorphs are sometimes found in other (noncoal) types of mining operations. Tridymite and cristobalite can be determined by analytical procedures similar to quartz, because they have their own spectroscopic and crystallographic properties.

Metals and their ores are examples of other candidate analytes. In regard to coal mines, airborne dust may be analyzed for metal content. This has been done for research purposes, to see if there is a correlation between metals in the dust and health effects. Some instances may involve the deliberate introduction of metals to aid a particular analytical goal. For example, if a coal mine has diesel machinery, it may be important to know which portion of the airborne dust comes from coal and which portion is diesel exhaust. Both are black dusts that are visually indistinguishable, but there are several ways to determine the relative dust proportions. One method involves measuring the metal content of the collected dust. Diesel fuel can be deliberately spiked with a metal-containing additive, for example zinc oxide added to the fuel as a catalyst. Therefore, if most of the zinc in a dust sample is known to originate from diesel particulates, and most of the iron in a sample is known to come from pyrite in the coal, then a means exists to differentiate the diesel and coal mass proportions based on these two metals. The diesel fuel could also be spiked with more novel catalysts, such as those containing cerium or platinum, at least in environments where the health risks presented by these metals could be minimized. Alternate metals in coal might also be suitable analytes.

A large number of metals and their ores are regarded as toxic, which makes it advantageous to be able to analyze dust samples for their presence. Lead and chromium, for example, may be found not only in mining or industrial processing operations but also in the dust of nonindustrial settings. The ore minerals may be measured by methods already discussed above. Fluorescence and phosphorescence spectroscopy might also used, although they are less commonly employed. After ashing or digestion, the metallic elements may be measured by a variety of techniques, which include both photometric and nonphotometric techniques. Mass spectrometry (MS), Atomic Absorption (AA), Inductively Coupled Plasma (ICP), coulometry, X-Ray Fluorescence (XRF), and Neutron Activation (NA) can all be used to measure metals, if the samples are prepared in one form or another, all commonly requiring ashing/digestion. Certainly many minerals and inorganic compounds could also be determined by Ultraviolet-Visible spectrometry (UV-Vis). Additionally, metal residue after ashing could be reacted with a chelating or complexing agent. Intense color is sometimes an attribute of the resultant materials, making them particularly suitable for UV-Vis assessment.

Another example of how these techniques could be used relates to environmental science. Airborne dust samples may be collected in a specific town, and minerals (clays, among others) and trace metals analysis can reveal the sources of dust. Examples of sources for such dust samples include mineral dust from local geology, windstorms in the Gobi desert, or volcanic eruptions in the Pacific Northwest United States. In another example, dust sampling is performed in urban homes. Detection of lead would reveal a health hazard and the TEOM time profile over the course of a day would detail when the dust exposure occurred.

Finally, for another example in an occupational setting, air samples are collected to assess employee exposure to powdered titanium dioxide ($TiO_2$) in a facility that bags and ships that material. Although $TiO_2$ exposure is not of great health concern, subsequent mineral and metals analysis can reveal the presence of an unexpected minor mineral (such as one of the crystalline silica polymorphs) or metal (heavy metal oxides, for example) contaminant to the dust that is of greater health concern than the $TiO_2$.

Some metal-containing complexes have paramagnetic properties. Electron Spin Resonance (ESR) spectroscopy or Electron Paramagnetic Resonance (EPR) spectroscopy are applicable for the detection and/or determination of this class of compounds, although these are somewhat less common methodologies.

Radioactive materials are also of interest for environmental sampling. The PDM filter assembly is sufficiently solid to possibly interfere with radioactivity counts. Its own structure would internally absorb some radiation from a sample, some particles being more easily stopped than others. If a radioactive ore or metal was the analyte of interest (polonium, for example), ashing the PDM filter could improve the accuracy of the radioassay. Therefore, collecting radioactive airborne dust with a PDM, ashing the filter, and then performing a radioassay on the residue permits a superior result as compared to prior techniques. Radioactivity is measured by a variety of methods. For purposes of our discussion, if X-ray emission is being measured, or light scintillation is part of the procedure, the method may be regarded as photometric. If particle emission is being measured and electrical pulse or current is part of the procedure, the method may be regarded as nonphotometric.

Examples of other analytical techniques that can be used with the disclosed methods are discussed in Principles of Instrumental Analysis, $2^{nd}$ Ed. D. A. Skoog and D. M. West (1980), and may also be found in other similar texts on analytical methods.

In view of the many possible embodiments to which the principles of our invention may be applied, it should be recognized that the illustrated embodiments are only preferred examples of the invention and should not be taken as a limitation on the scope of the invention. Rather, the scope of the invention is defined by the following claims. We therefore claim as our invention all that comes within the scope and spirit of these claims.

APPENDIX OF TABLES

TABLE I

| | | P-7 Analysis of Ashed Candidate Filter Materials | | | | | |
|---|---|---|---|---|---|---|---|
| Filter Material | Sample ID | Integr. Abs. 917 cm$^{-1}$ | Kaolin Mass (µg) | Integr. Abs. 800 cm$^{-1}$ | Quartz Mass (µg) | \|Quartz Mass\| Avg. (µg) | Est. LOQ[4] (µg) |
| PVCA membrane | dm4501 | 0.0117 | 0.5 | 0.0323 | 0.6 | 0.4 | 4 |
| | dm4502 | 0.0061 | 0.3 | 0.0195 | 0.4 | | |
| | dm4503 | 0.0045 | 0.2 | −0.0013 | −0.1 | | |
| PVC membrane | gla2k0 | 0.0079 | 0.3 | 0.0158 | 0.3 | 0.6 | 6 |
| | gla2k4 | 0.0045 | 0.2 | 0.0170 | 0.3 | | |
| | gla2k7 | 0.0050 | 0.2 | 0.0613 | 1.2 | | |
| | gla2k9 | 0.0010 | 0.0 | 0.0208 | 0.4 | | |
| White PP ring/base | wrb9 | −0.0422 | −1.8 | −0.7812 | −15.4 | 22.5 | 225 |
| Pairs with $TiO_2$ | wrb10 | −0.0468 | −2.0 | −0.8371 | −16.5 | | |
| | wrb11 | −0.0509 | −2.2 | −1.7969 | −35.7 | | |
| Clear PP | crb10 | 0.0091 | 0.4 | 0.0048 | 0.0 | 0.3 | 3 |
| Ring/base pairs | crb11 | 0.0121 | 0.5 | 0.0249 | 0.4 | | |
| | crb12 | −0.0056 | −0.2 | 0.0174 | 0.4 | | |
| High wt. PP | bmf40c1 | −0.0057 | −0.2 | −0.0096 | −0.2 | 0.1 | 1 |
| Electret | bmf40c2 | 0.0053 | 0.2 | 0.0061 | 0.1 | | |
| Blown melt fiber | bmf40c3 | 0.0073 | 0.3 | 0.0058 | 0.1 | | |
| Med wt. PP | bmf30f1 | 0.0129 | 0.6 | −0.0057 | −0.2 | 0.3 | 3 |
| Electret | bmf30f2 | 0.0088 | 0.4 | 0.0156 | 0.3 | | |
| Blown melt fiber | bmf30f3 | 0.0147 | 0.6 | 0.0233 | 0.4 | | |
| Spun bound cover | 2sbc1 | 0.0191 | 0.8 | −0.1744 | −3.6 | 2.9 | 29 |

TABLE I-continued

P-7 Analysis of Ashed Candidate Filter Materials

| Filter Material | Sample ID | Integr. Abs. 917 cm$^{-1}$ | Kaolin Mass (μg) | Integr. Abs. 800 cm$^{-1}$ | Quartz Mass (μg) | \|Quartz Mass\| Avg. (μg) | Est. LOQ[A] (μg) |
|---|---|---|---|---|---|---|---|
| For electret with TiO$_2$ | 2sbc1b | 0.0052 | 0.2 | −0.1607 | −3.2 | | |
| | 2sbc2 | 0.0067 | 0.3 | −0.0921 | −1.9 | | |
| Non-woven cover | t31511 | 0.0112 | 0.5 | 0.0045 | 0.0 | 0.0 | 0 |
| For electret | t31512 | 0.0343 | 1.5 | 0.0119 | 0.0 | | |
| | t31513 | 0.0021 | 0.1 | −0.0025 | −0.1 | | |
| All-nylon | no25b1 | −0.0108 | −0.5 | 0.0482 | 1.0 | 1.3 | 13 |
| Fibrous filter | no25b2 | −0.0102 | −0.4 | 0.0368 | 0.8 | | |
| | no25b3 | −0.0133 | −0.6 | 0.0973 | 2.0 | | |
| HEPA all-nylon | n030a1 | −0.0299 | −1.3 | −0.0124 | −0.1 | 0.5 | 5 |
| Fibrous filter | n030a2 | 0.0460 | 2.0 | 0.0378 | 0.5 | | |
| | n030a3 | 0.0021 | 0.1 | 0.0502 | 1.0 | | |
| Cellulose with | cmace1 | 0.0084 | 0.4 | 0.0221 | 0.4 | 0.5 | 5 |
| Melamine binder | cmace2 | 0.0086 | 0.4 | 0.0310 | 0.6 | | |
| | cmace3 | 0.0064 | 0.3 | 0.0227 | 0.4 | | |
| High strength | cwg411 | −0.0012 | −0.1 | 0.0251 | 0.5 | 0.2 | 2 |
| Cellulose | cwg412 | 0.0040 | 0.2 | 0.0096 | 0.2 | | |
| | cwg413 | −0.0008 | 0.0 | 0.0000 | 0.0 | | |

[A] 10 × Avg|Quartz Mass|

TABLE II

Open-Face Sample Gravimetric and Spectrometric Results

| Sample No. | Grav. Quartz Mass (μg) | 0.942 Corrected Grav. Mass (μg) | Spectral Reference = PVCA Filter | | | Spectral Reference = PVCA + PDM Filters | | |
|---|---|---|---|---|---|---|---|---|
| | | | P-7 Quartz (μg) | Difference (μg) | Percent Equiv. | P-7 Quartz (μg) | Difference (μg) | Percent Equiv. |
| Polyester-Back | | | | | | | | |
| P7 | 529 | 498 | 495 | −3 | −0.7 | 489 | −9 | −1.9 |
| P8 | 514 | 484 | 495 | 11 | 2.2 | 485 | 1 | 0.2 |
| P9 | 514 | 484 | 485 | 1 | 0.2 | 482 | −2 | −0.5 |
| P10 | 512 | 482 | 474 | −8 | −1.7 | 472 | −10 | −2.1 |
| P11 | 524 | 494 | 491 | −3 | −0.5 | 489 | −5 | −0.9 |
| P12 | 517 | 487 | 496 | 9 | 1.8 | 492 | 5 | 1.0 |
| P13 | 495 | 466 | 492 | 26 | 5.5 | 487 | 21 | 4.4 |
| P14 | 498 | 469 | 466 | −3 | −0.7 | 457 | −12 | −2.6 |
| P15 | 501 | 472 | 482 | 10 | 2.1 | 483 | 11 | 2.3 |
| P16 | 513 | 483 | 495 | 12 | 2.4 | 495 | 12 | 2.4 |
| Means = | 511.7 | 482.0 | 487.1 | 5.1 | 1.1 | 483.1 | 1.1 | 0.2 |
| 95 Pct. Conf. Intervals for Mean Diff. = | | | | −2.2 to 12.4 SD = 10.2 | −0.5 to 2.6 RSD = 2.1 | | −6.7 to 8.9 SD = 10.9 | −1.4 to 1.8 RSD = 2.3 |
| Cellulose-Back | | | | | | | | |
| C7 | 497 | 468 | 465 | −3 | −0.7 | 467 | −1 | −0.3 |
| C8 | 498 | 469 | 461 | −8 | −1.7 | 462 | −7 | −1.5 |
| C9 | 491 | 463 | 456 | −7 | −1.4 | 456 | −7 | −1.4 |
| C10 | 487 | 459 | 461 | 2 | 0.5 | 461 | 2 | 0.5 |
| C11 | 539 | 508 | 499 | −9 | −1.7 | 501 | −7 | −1.3 |
| C12 | 488 | 460 | 448 | −12 | −2.5 | 449 | −11 | −2.3 |
| C13 | 487 | 459 | 460 | 1 | 0.3 | 459 | 0 | 0.1 |
| C14 | 484 | 456 | 458 | 2 | 0.5 | 458 | 2 | 0.5 |
| C15 | 490 | 462 | 483 | 21 | 4.6 | 486 | 24 | 5.3 |
| C16 | 539 | 508 | 504 | −4 | −0.7 | 503 | −5 | −0.9 |
| Means = | 500.0 | 471.0 | 469.5 | −1.5 | −0.3 | 470.2 | −0.8 | −0.1 |
| 95 Pct. Conf. Intervals for Mean Diff. = | | | | −8.2 to 5.2 SD = 9.4 | −1.7 to 1.1 RSD = 2.0 | | −7.9 to 6.3 SD = 9.9 | −1.7 to 1.3 RSD = 2.1 |

TABLE III

Cellulose-Back and PVC Filter P-7 Comparison Analyses

| Test No. | PVC Filter No. | PVC Filter P-7 Quartz Mass (μg) | PDM & Filter Nos. | PDM Filter P-7 Quartz Mass (μg) | PDM-PVC$_M$ Quartz Mass (μg) | PDM-PVC$_M$ Quartz Percent Equiv. |
|---|---|---|---|---|---|---|
| 1 | HC13 | 445 | | | | |
| 1 | HC14 | 434 | 1-2C13 | 451 | 7 | 1.7 |
| 1 | HC15 | 441 | 2-2C14 | 451 | 7 | 1.5 |
| 1 | HC15B | 455 | 3-2C15 | 435 | −9 | −2.1 |
| | Mean = | 443.8 | | 445.5 | 1.7 | 0.4 |
| | | | | S.D. = | 9.4 | 2.1 |
| 2 | HC16 | 489 | | | | |
| 2 | HC17 | 476 | 1-2C16 | 448 | −23 | −4.8 |
| 2 | HC18 | 475 | 2-2C17 | 466 | −5 | −1.1 |
| 2 | HC18B | 443 | 3-2C18 | 460 | −11 | −2.3 |
| | Mean = | 470.9 | | 458.0 | −12.9 | −2.7 |
| | | | | S.D. = | 8.9 | 1.9 |
| 3 | HC19 | 402 | | | | |
| 3 | HC20 | 419 | 1-2C19 | 408 | −2 | −0.5 |
| 3 | HC21 | 408 | 2-2C20 | 417 | 6 | 1.6 |
| 3 | HC21B | 412 | 3-2C21 | 413 | 3 | 0.7 |
| | Mean = | 410.2 | | 412.6 | 2.4 | 0.6 |
| | | | | S.D. = | 4.2 | 1.0 |
| 4 | HC22 | 430 | | | | |
| 4 | HC23 | 452 | 1-2C22 | 422 | −15 | −3.5 |
| 4 | HC24 | 430 | 2-2C23 | 436 | −1 | −0.3 |
| 4 | HC24B | 438 | 3-2C24 | 432 | −5 | −1.3 |
| | Mean = | 437.5 | | 430.0 | −7.4 | −1.7 |
| | | | | S.D. = | 7.2 | 1.6 |
| 5 | HC25 | 446 | | | | |
| 5 | HC26 | 450 | 1-2C25 | 443 | −11 | −2.4 |
| 5 | HC27 | 471 | 2-2C26 | 449 | −5 | −1.0 |
| 5 | HC27B | 450 | 3-2C27 | 428 | −26 | −5.7 |
| | Mean = | 454.1 | | 440.3 | −13.8 | −3.0 |
| | | | | S.D. = | 10.8 | 2.4 |
| 6 | HC28 | 447 | | | | |
| 6 | HC29 | 449 | 1-2C28 | 432 | −12 | −2.6 |
| 6 | HC30 | 440 | 2-2C29 | 442 | −2 | −0.4 |
| 6 | HC30B | 437 | 3-2C30 | 446 | 2 | 0.5 |
| | Mean = | 443.5 | | 439.7 | −3.8 | −0.9 |
| | | | | S.D. = | 7.1 | 1.6 |
| | Summary Mean = | | | | −5.6 | −1.2 |
| | 95 Pct Conf. Intervals for Mean Diff. = | | | | −10.4 to −0.9 | −2.3 to −0.2 |
| | Summary S.D. = | | | | 9.5 | 2.1 |

TABLE IV

Polyester-Back and PVC Filter P-7 Comparison Analyses

| Test No. | PVC Filter No. | PVC Filter P-7 Quartz Mass (μg) | PDM & Filter Nos. | PDM Filter P-7 Quartz Mass (μg) | PDM-PVC$_M$ Quartz Mass (μg) | PDM-PVC$_M$ Quartz Percent Equiv. |
|---|---|---|---|---|---|---|
| 7 | HP13 | 453 | | | | |
| 7 | HP14 | 448 | 1-2P13 | 451 | 2 | 0.5 |
| 7 | HP15 | 443 | 2-2P14 | 452 | 4 | 0.8 |
| 7 | HP15B | 449 | 3-2P15 | 418 | −31 | −6.9 |
| | Mean = | 448.5 | | 440.2 | −8.3 | −1.9 |
| | | | | S.D. = | 19.6 | 4.4 |
| 8 | HP16 | 458 | | | | |
| 8 | HP17 | 474 | 1-2P16 | 433 | −24 | −5.2 |
| 8 | HP18 | 438 | 2-2P17 | 462 | 6 | 1.3 |
| 8 | HP18B | 456 | 3-2P18 | 420 | −36 | −7.9 |
| | Mean = | 456.2 | | 438.2 | −18.0 | −3.9 |
| | | | | S.D. = | 21.6 | 4.7 |
| 9 | HP19 | 454 | | | | |
| 9 | HP20 | 448 | 1-2P19 | 422 | −29 | −6.5 |
| 9 | HP21 | 451 | 2-2P20 | 447 | −4 | −0.9 |
| 9 | HP21B | 452 | 3-2P21 | 444 | −8 | −1.7 |
| | Mean = | 451.4 | | 437.6 | −13.7 | −3.0 |
| | | | | S.D. = | 13.6 | 3.0 |
| 10 | HP22 | 463 | | | | |
| 10 | HP23 | 447 | 1-2P22 | 467 | 14 | 3.0 |
| 10 | HP24 | 457 | 2-2P23 | 466 | 12 | 2.7 |

TABLE IV-continued

Polyester-Back and PVC Filter P-7 Comparison Analyses

| Test No. | PVC Filter No. | PVC Filter P-7 Quartz Mass (µg) | PDM & Filter Nos. | PDM Filter P-7 Quartz Mass (µg) | PDM-PVC$_M$ Quartz Mass (µg) | PDM-PVC$_M$ Quartz Percent Equiv. |
|---|---|---|---|---|---|---|
| 10 | HP24B | 447 | 3-2P24 | N/A | N/A | N/A |
|  | Mean = | 453.5 |  | 466.5 | 13.0 | 2.9 |
|  |  |  |  | S.D. = | 0.8 | 0.2 |
| 11 | HP25 | 439 |  |  |  |  |
| 11 | HP26 | 431 | 1-2P25 | 413 | −17 | −4.0 |
| 11 | HP27 | 422 | 2-2P26 | 428 | −2 | −0.4 |
| 11 | HP27B | 428 | 3-2P27 | 417 | −13 | −3.1 |
|  | Mean = | 429.9 |  | 419.1 | −10.8 | −2.5 |
|  |  |  |  | S.D. = | 8.1 | 1.9 |
| 12 | HP28 | 431 |  |  |  |  |
| 12 | HP29 | 469 | 1-2P28 | 460 | 11 | 2.5 |
| 12 | HP30 | 451 | 2-2P29 | 449 | 0 | 0.1 |
| 12 | HP30B | 445 | 3-2P30 | 445 | −4 | −0.8 |
|  | Mean = | 448.8 |  | 451.5 | 2.8 | 0.6 |
|  |  |  |  | S.D. = | 7.8 | 1.7 |
|  | Summary Mean = |  |  |  | −6.9 | −1.6 |
|  | 95 Pct. Conf. Intervals for Mean Diff. = |  |  |  | −15.0 to 1.0 | −3.3 to 0.2 |
|  | Summary S.D. = |  |  |  | 15.7 | 3.5 |

TABLE V

Cellulose-Back and PVC Filter Collected Mass Comparisons

| Test No. | PVC Filter No. | PVC Filter Grav. Mass (µg) | PDM & Filter Nos. | PDM EOF Mass (µg) | PDM Filter Grav. Mass (µg) | PDM/PVC$_M$ Filter Grav. Diff. (Pct.) | EOF/PVC$_M$ Diff. (Pct.) | EOF/PDM$_{Grav}$ Diff. (Pct.) |
|---|---|---|---|---|---|---|---|---|
| 1 | HC13 | 482 |  |  |  |  |  |  |
| 1 | HC14 | 460 | 1-2C13 | 517 | 469 | −1.6 | 8.5 | 10.2 |
| 1 | HC15 | 490 | 2-2C14 | 529 | 476 | −0.1 | 11.0 | 11.1 |
| 1 | HC15B | 474 | 3-2C15 | 546 | 475 | −0.3 | 14.6 | 14.9 |
|  | Mean = | 476.5 |  | 530.7 | 473.3 | −0.7 | 11.4 | 12.1 |
|  |  |  |  |  | S.D. = | 0.8 | 3.1 | 2.5 |
| 2 | HC16 | 518 |  |  |  |  |  |  |
| 2 | HC17 | 507 | 1-2C16 | 537 | 468 | −6.1 | 7.7 | 14.7 |
| 2 | HC18 | 498 | 2-2C17 | 548 | 489 | −1.9 | 9.9 | 12.1 |
| 2 | HC18B | 471 | 3-2C18 | 598 | 476 | −4.5 | 20.0 | 25.6 |
|  | Mean = | 498.5 |  | 561.0 | 477.7 | −4.2 | 12.5 | 17.4 |
|  |  |  |  |  | S.D. = | 2.1 | 6.5 | 7.2 |
| 3 | HC19 | 432 |  |  |  |  |  |  |
| 3 | HC20 | 463 | 1-2C19 | 459 | 426 | −3.9 | 3.6 | 7.7 |
| 3 | HC21 | 434 | 2-2C20 | 467 | 426 | −3.9 | 5.4 | 9.6 |
| 3 | HC21B | 444 | 3-2C21 | 520 | 427 | −3.7 | 17.3 | 21.8 |
|  | Mean = | 443.3 |  | 482.0 | 426.3 | −3.8 | 8.7 | 13.1 |
|  |  |  |  |  | S.D. = | 0.1 | 7.5 | 7.6 |
| 4 | HC22 | 463 |  |  |  |  |  |  |
| 4 | HC23 | 468 | 1-2C22 | 458 | 455 | −2.0 | −1.4 | 0.7 |
| 4 | HC24 | 458 | 2-2C23 | 487 | 472 | 1.6 | 4.8 | 3.2 |
| 4 | HC24B | 469 | 3-2C24 | 537 | 467 | 0.5 | 15.6 | 15.0 |
|  | Mean = | 464.5 |  | 494.0 | 464.7 | 0.0 | 6.4 | 6.3 |
|  |  |  |  |  | S.D. = | 1.9 | 8.6 | 7.7 |
| 5 | HC25 | 475 |  |  |  |  |  |  |
| 5 | HC26 | 469 | 1-2C25 | 501 | 496 | 4.3 | 5.3 | 1.0 |
| 5 | HC27 | 485 | 2-2C26 | 495 | 483 | 1.5 | 4.0 | 2.5 |
| 5 | HC27B | 474 | 3-2C27 | 543 | 465 | −2.3 | 14.1 | 16.8 |
|  | Mean = | 475.8 |  | 513.0 | 481.3 | 1.2 | 7.8 | 6.6 |
|  |  |  |  |  | S.D. = | 3.3 | 5.5 | 8.7 |
| 6 | HC28 | 477 |  |  |  |  |  |  |
| 6 | HC29 | 464 | 1-2C28 | 486 | 443 | −5.4 | 3.8 | 9.7 |
| 6 | HC30 | 467 | 2-2C29 | 500 | 447 | −4.5 | 6.8 | 11.9 |
| 6 | HC30B | 465 | 3-2C30 | 568 | 450 | −3.9 | 21.3 | 26.2 |
|  | Mean = | 468.3 |  | 518.0 | 446.7 | −4.6 | 10.6 | 16.0 |
|  |  |  |  |  | S.D. = | 0.8 | 9.4 | 9.0 |
|  | Summary Mean = |  |  |  |  | −2.0 | 9.6 | 11.9 |
|  | 95 Pct. Conf. Interval for Mean Diff. = |  |  |  |  | −3.4 to −0.6 | 6.4 to 12.7 | 8.2 to 15.7 |
|  | Summary S.D. = |  |  |  |  | 2.8 | 6.3 | 7.6 |
|  | Summary Mean w/o Unit 3 = |  |  |  |  | −1.8 | 5.8 | 7.9 |
|  | 95 Pct. Conf. Interval for Mean Diff. w/o Unit 3 = |  |  |  |  | −3.8 to 0.2 | 3.7 to 7.9 | 4.8 to 10.9 |
|  | Summary S.D. w/o Unit 3 = |  |  |  |  | 3.2 | 3.3 | 4.8 |

TABLE VI

Polyester-Back and PVC Filter Collected Mass Comparisons

| Test No. | PVC Filter No. | PVC Filter Grav. Mass (μg) | PDM & Filter Nos. | PDM EOF Mass (μg) | PDM Filter Grav. Mass (μg) | PDM/PVC$_M$ Filter Grav. Diff. (Pct.) | EOF/PVC$_M$ Diff. (Pct.) | EOF/PDM$_{Grav}$ Diff. (Pct.) |
|---|---|---|---|---|---|---|---|---|
| 7 | HP13 | 475 | | | | | | |
| 7 | HP14 | 462 | 1-2P13 | 512 | 495 | 5.4 | 9.1 | 3.4 |
| 7 | HP15 | 467 | 2-2P14 | 513 | 494 | 5.2 | 9.3 | 3.8 |
| 7 | HP15B | 474 | 3-2P15 | 547 | 473 | 0.7 | 16.5 | 15.6 |
| | Mean = | 469.5 | | 524.0 | 487.3 | 3.8 | 11.6 | 7.5 |
| | | | | S.D. = | | 2.6 | 4.2 | 6.9 |
| 8 | HP16 | 482 | | | | | | |
| 8 | HP17 | 491 | 1-2P16 | 494 | 484 | 1.1 | 3.2 | 2.1 |
| 8 | HP18 | 463 | 2-2P17 | 533 | 509 | 6.3 | 11.3 | 4.7 |
| 8 | HP18B | 479 | 3-2P18 | 562 | 467 | −2.5 | 17.4 | 20.3 |
| | Mean = | 478.8 | | 529.7 | 486.7 | 1.7 | 10.6 | 8.8 |
| | | | | S.D. = | | 4.4 | 7.1 | 9.9 |
| 9 | HP19 | 471 | | | | | | |
| 9 | HP20 | 456 | 1-2P19 | 496 | 472 | 0.7 | 5.9 | 5.1 |
| 9 | HP21 | 479 | 2-2P20 | 499 | 479 | 2.2 | 6.5 | 4.2 |
| 9 | HP21B | 468 | 3-2P21 | 564 | 490 | 4.6 | 20.4 | 15.1 |
| | Mean = | 468.5 | | 519.7 | 480.3 | 2.5 | 10.9 | 8.2 |
| | | | | S.D. = | | 1.9 | 8.2 | 6.1 |
| 10 | HP22 | 487 | | | | | | |
| 10 | HP23 | 472 | 1-2P22 | 521 | 510 | 4.7 | 7.0 | 2.2 |
| 10 | HP24 | 490 | 2-2P23 | 519 | 503 | 3.3 | 6.6 | 3.2 |
| 10 | HP24B | 499 | 3-2P24 | N/A | N/A | N/A | N/A | N/A |
| | Mean = | 487.0 | | 520.0 | 506.5 | 4.0 | 6.8 | 2.7 |
| | | | | S.D. = | | 1.0 | 0.3 | 0.7 |
| 11 | HP25 | 457 | | | | | | |
| 11 | HP26 | 448 | 1-2P25 | 463 | 457 | 1.0 | 2.3 | 1.3 |
| 11 | HP27 | 448 | 2-2P26 | 485 | 463 | 2.3 | 7.2 | 4.8 |
| 11 | HP27B | 457 | 3-2P27 | 540 | 448 | −1.0 | 19.3 | 20.5 |
| | Mean = | 452.5 | | 496.0 | 456.0 | 0.8 | 9.6 | 8.8 |
| | | | | S.D. = | | 1.7 | 8.8 | 10.3 |
| 12 | HP28 | 481 | | | | | | |
| 12 | HC29 | 484 | 1-2P28 | 510 | 503 | 4.5 | 6.0 | 1.4 |
| 12 | HP30 | 486 | 2-2P29 | 503 | 491 | 2.0 | 4.5 | 2.4 |
| 12 | HP30B | 474 | 3-2P30 | 551 | 480 | −0.3 | 14.5 | 14.8 |
| | Mean = | 481.3 | | 521.3 | 491.3 | 2.1 | 8.3 | 6.1 |
| | | | | S.D. = | | 2.4 | 5.4 | 7.5 |
| | Summary Mean = | | | | | 2.4 | 9.8 | 7.4 |
| | 95 Pct. Conf. Interval for Mean Diff. = | | | | | 1.1 to 3.6 | 6.9 to 12.8 | 3.8 to 10.9 |
| | Summary S.D. = | | | | | 2.5 | 5.7 | 6.9 |
| | Summary Mean w/o Unit 3 = | | | | | 3.2 | 6.6 | 3.2 |
| | 95 Pct. Conf. Interval for Mean Diff. w/o Unit 3 = | | | | | 2.0 to 4.4 | 5.0 to 8.2 | 2.4 to 4.1 |
| | Summary S.D. w/o Unit 3 = | | | | | 1.9 | 2.5 | 1.3 |

TABLE VII

Filter Composition-Specific Standard Deviations for Zero-Mass Tests (μg)

| Filter Composition | Test No. | PDM Unit 115 | PDM Unit 120 | PDM Unit 125 | PDM Unit 127 | Composition Means | Range of Values |
|---|---|---|---|---|---|---|---|
| Standard Fiberglass Filters | Test 1 | | 0.35 | | | 0.28 | 0.24-0.35 |
| | Test 2 | | | 0.28 | | | |
| | Test 3 | 0.25 | | | 0.28 | | |
| | Test 4 | 0.24 | | | | | |
| Polyester-Back Nylon Filters | Test 1 | 0.27 | | | 0.36 | 0.31 | 0.25-0.36 |
| | Test 2 | | 0.34 | | | | |
| | Test 3 | | | 0.28 | | | |
| | Test 4 | | 0.35 | | 0.25 | | |
| Cellulose-Back Nylon Filters | Test 1 | | | 0.38 | | 0.31 | 0.21-0.38 |
| | Test 2 | 0.31 | | | 0.21 | | |
| | Test 3 | | 0.37 | | | | |
| | Test 4 | | | | 0.28 | | |
| PDM Unit Means = | | 0.27 | 0.35 | 0.30 | 0.28 | | |
| Range of Values = | | 0.24-0.31 | 0.34-0.37 | 0.25-0.38 | 0.21-0.36 | | |

Overall Mean = 0.30
Overall Range of Values = 0.21-0.38

TABLE VIII

| Test-Specific Mean Standard Deviations for Zero Mass Tests (µg) | | | | |
| --- | --- | --- | --- | --- |
|  | Test 1 | Test 2 | Test 3 | Test 4 |
| Means = | 0.34 | 0.29 | 0.30 | 0.28 |
| Range of Values = | 0.27-0.38 | 0.21-0.34 | 0.25-0.37 | 0.24-0.35 |

I claim:

1. A method of determining a mass of dust and determining at least one component of the dust, the method comprising:
providing a monitor comprising a housing that houses a mass determination device within the housing that collects dust on a filter to substantially continuously determine a mass of dust collected by the filter, wherein the mass determination device comprises a tapered element oscillating microbalance (TEOM) that oscillates the filter at a resonance frequency that changes in response to increased mass on the filter and determining the mass comprises quantitating a change in the resonance frequency, the monitor defining an airflow pathway from an environment into the housing and through the filter, wherein the filter consists essentially of organic polymeric material that is ashable for instrumental analysis and is substantially free of glass, quartz fiber, polytetrafluoroethylene (PTFE), and titanium dioxide, the organic polymeric material comprising a non-shedding fibrous construction;
collecting dust particles from the air that moves along the pathway and through the filter and substantially continuously determining with the mass determination device the mass of dust collected on the filter; and
removing the filter from the monitor, ashing the filter, and subjecting the ashed filter to an instrumental analysis for determining at least one component of the dust.

2. The method of claim 1, wherein determining the mass further comprises applying a filter composition-specific mass correction function to compensate for changes in the mass determination not caused by collected dust.

3. The method of claim 1, wherein ashing the filter is selected from the group consisting of thermal ashing, microwave ashing, low temperature ashing, and chemical digestion.

4. The method of claim 1, wherein the filter is mounted to a non-filtration mechanical support that does not collect and retain dust, and removing the filter from the monitor comprises removing the support with the filter mounted to the support, wherein the support consists essentially of organic material that is ashable for instrumental analysis, and ashing the filter comprises ashing the filter together with the non-filtration mechanical support for combined instrumental analysis.

5. The method of claim 1, wherein the instrumental analysis comprises a spectroscopic analysis.

6. The method of claim 5, wherein the spectroscopic analysis comprises subjecting the filter to infrared absorbance spectrometric analysis for quartz that determines a quantity of quartz present on the filter.

7. The method of claim 1, further comprising heating air to a constant temperature and substantially continuously sensing changes in humidity in the airflow pathway within the monitor, and responsive to changes in humidity in the airflow pathway substantially continuously correcting the determination of mass detected on the filter to compensate for changes in mass of moisture from the airflow present on the filter.

8. The method of claim 7, wherein the filter is not hydrophobic and correcting the determination of mass comprises applying a filter composition-specific humidity correction factor, wherein the humidity correction factor is empirically derived from monitor mass response when sampling clean air, the internal filter is exposed in situ to different airflow relative humidity levels within the monitor, and the relative humidity levels within the monitor are measured by the monitor also.

9. The method of claim 4, further comprising placing the filter in a substantially dust-tight non-filter receptacle for the filter once the filter is removed from the monitor and until the filter is subjected to the instrumental analysis, wherein the non-filter receptacle comprises an ashable polymeric container, and ashing the filter comprises ashing the filter with the non-filter receptacle.

10. The method of claim 4, further comprising placing the filter in a substantially dust-tight receptacle for the filter once the filter is removed from the monitor and until the filter is subjected to the instrumental analysis, wherein the receptacle comprises a substantially rigid filter-immobilizing and surfactant-resistant rinsable container that restricts dust drift within the container, removing the filter from the container without using a tool, and once the filter is removed from the container, the container is rinsed prior to analysis of the filter to remove and include container-retained dust in the analysis.

11. The method of claim 1, wherein the instrumental analysis comprises a nonphotometric analysis, wherein the nonphotometric analysis is selected from the group consisting of mass spectrometry, coulometry, and particle radiometric analysis.

12. The method of claim 1, wherein the filter comprises filters of more than one type, wherein the monitor is adapted to identify the type of filter placed within the monitor, based on filter properties alone.

13. The method of claim 12, wherein the monitor is adapted to identify the filter type from the oscillation frequency at the beginning of filter use, wherein the monitor is further adapted to automatically initiating variations in features of operation suitable for the filter type identified.

14. The method of claim 1, wherein the filter comprises filters of more than one type, wherein the monitor is adapted to identify the type of filter placed within the monitor based on a singular user input at the time of monitor use, and changes in monitor operation to suitably utilize a filter type are implemented automatically solely from the singular user input for selection of filter type in monitor control software at the time of monitor use.

15. A dust monitor, comprising:
a housing;
a mass determination device within the housing that collects dust on a filter to substantially continuously determine a mass of dust collected by the filter, the mass determination device comprising a tapered element oscillating microbalance (TEOM) that oscillates the filter at a resonance frequency that changes in response to increased mass on the filter; and
an airflow pathway into the housing and through the filter, wherein the filter consists essentially of organic polymeric material that is ashable for instrumental analysis and is substantially free of glass, quartz fiber, polytetrafluoroethylene (PTFE), and titanium dioxide, and the filter collects particulates from the air that moves along the pathway and through the filter, the organic polymeric material comprising a non-shedding fibrous construction.

16. The dust monitor of claim 15, wherein the filter has a surface exposed to the airflow pathway and is mounted to a non-filtration mechanical support that oscillates the filter and is removable from the housing, wherein the non-filtration mechanical support has an outlet opening that is removably mounted to the TEOM and defines an enclosed air passageway that directs air flowing through the filter to flow into the TEOM, the outlet opening being substantially smaller than the surface of the filter exposed to the airflow pathway such that the air passageway in the non-filtration mechanical support has a cross-section that reduces in size from the filter to the outlet, and the non-filtration mechanical support consists essentially of organic polymeric material that is jointly ashable with the filter for a combined instrumental analysis of the filter and non-filtration mechanical support.

17. The dust monitor of claim 15, wherein the organic polymeric material is nonwoven, and is selected from the group consisting of polyvinyl chloride, polyvinyl chloride/acrylic copolymer, polypropylene, polyethylene, polyester, and nylon.

18. The dust monitor of claim 15, wherein the filter is not hydrophobic, and the monitor further comprises an air heating means with a temperature sensing means to maintain a constant airflow pathway temperature and a humidity sensing means for the airflow pathway within the monitor, wherein the mass determination device is adapted to substantially continuously correct the determined mass of dust to compensate for the presence of moisture collected on the filter by applying a filter composition-specific humidity correction factor to correct the determined mass of dust for changes in humidity of the air in the airflow pathway from a reference humidity value.

19. The dust monitor of claim 15 further comprising a substantially dust-tight receptacle for the filter once the filter is removed from the housing, wherein the receptacle enables dust preservation by subsequent transfer of the filter into an ashing procedure without using a tool.

20. The dust monitor of claim 15 further comprising filters of more than one type having different color markings for each type of filter, wherein the different color markings comprise organic ashable pigment in at least one filter component.

21. The dust monitor of claim 15 further comprising filters of more than one type having different color markings for each type of filter, wherein the different color markings comprise organic ashable dye in at least one filter component, wherein the organic ashable dye has a molecular structure that is free of metals.

22. The dust monitor of claim 15 further comprising filters of more than one type and removable resonance frequency microbalance modules of more than one type for suitable operation with the filters of more than one type, wherein the removable resonance frequency microbalance modules further comprise either physical or electronic means for identifying them to the monitor; wherein the monitor is adapted to interact with and identify the microbalance modules and automatically initiate differing features of operation suitable for the module type and related filter type identified.

23. The dust monitor of claim 19, wherein the receptacle consists essentially of organic, ashable material.

24. The dust monitor of claim 19, wherein the receptacle comprises a substantially rigid container adapted to immobilize a filter positioned in the container, the container having surfactant resistant rinsable inner surface.

25. A dust monitor, comprising:
a housing;
a filter that collects dust from air flowing into the housing and through the filter;
a resonance frequency microbalance within the housing, wherein the resonance frequency microbalance comprises a tapered element oscillating microbalance (TEOM) that oscillates the filter at a resonance frequency that changes in response to increased mass on the filter;
the filter consisting essentially of an ashable organic polymeric material and is substantially free of glass, quartz fiber, polytetrafluoroethylene (PTFE), and titanium dioxide; and
wherein the filter is mounted to a non-filtration mechanical support that has an outlet opening that is removably mounted to the TEOM and defines an enclosed air passageway that directs air flowing through the filter to flow into the TEOM, and the non-filtration mechanical support consists essentially of organic polymeric material that is jointly ashable with the filter for a combined instrumental analysis of the filter and non-filtration mechanical support.

26. A method of determining a mass of dust and determining at least one component of the dust, the method comprising:
providing the dust monitor of claim 15;
collecting dust particles from the air that moves along the pathway and through the filter and substantially continuously determining with the TEOM the mass of dust collected on the filter; and
removing the filter from the monitor, ashing the filter, and subjecting the ashed filter to an instrumental analysis for determining at least one component of the dust.

27. A method of determining a mass of dust and determining at least one component of the dust, the method comprising:
providing the dust monitor of claim 25;
collecting dust particles from the air flowing into the housing and through the filter and substantially continuously determining with the TEOM the mass of dust collected on the filter; and
removing the filter and the non-filtration mechanical support from the monitor, ashing the filter and the non-filtration mechanical support, and subjecting the ashed filter and non-filtration mechanical support to an instrumental analysis for determining at least one component of the dust.

* * * * *

UNITED STATES PATENT AND TRADEMARK OFFICE
CERTIFICATE OF CORRECTION

PATENT NO.         : 7,947,503 B2
APPLICATION NO.    : 11/922381
DATED              : May 24, 2011
INVENTOR(S)        : Donald P. Tuchman It is certified that error appears in the above-identified patent and that said Letters Patent is hereby corrected as shown below:

In the Specification:

Column 11, line 62, "IR)" should be --(IR)--

Column 17, line 17, "24 mg/m$^3$" should be --2-4 mg/m$^3$--

Column 21, line 47, "$M_t = K_0 \times [1/(F_t)^2/(F_0)^2] - H_t$"
should be --$M_t = K_0 \times [1/(F_t)^2 - 1/(F_0)^2] - H_t$--

Column 21, line 59, "$T_O$ time t" should be --$T_O$ to time t--

Column 23, line 45, "$M_t = K_0 \times [1/(F_t)^2/(F_0)^2] - [C \times (R_t - R_0)]$"
should be --$M_t = K_0 \times [1/(F_t)^2 - 1/(F_0)^2] - [C \times (R_t - R_0)]$--

Column 30, line 17, "stern," should be --stem,--

Column 32, line 38, "sane" should be --same--

Signed and Sealed this
Tenth Day of January, 2012

David J. Kappos
*Director of the United States Patent and Trademark Office*